(12) United States Patent
Cohen

(10) Patent No.: US 12,201,632 B2
(45) Date of Patent: Jan. 21, 2025

(54) LEVOKETOCONAZOLE FOR TREATMENT OF CONGENITAL ADRENAL HYPERPLASIA AND PRIMARY ALDOSTERONISM

(71) Applicant: Strongbridge Dublin Limited, Chicago, IL (US)

(72) Inventor: Fred Cohen, Washington Crossing, PA (US)

(73) Assignee: STRONGBRIDGE DUBLIN LIMITED, Dublin (IE)

( * ) Notice: Subject to any disclaimer, the term of this patent is extended or adjusted under 35 U.S.C. 154(b) by 873 days.

(21) Appl. No.: 17/226,640

(22) Filed: Apr. 9, 2021

(65) Prior Publication Data

US 2021/0220352 A1    Jul. 22, 2021

Related U.S. Application Data

(63) Continuation of application No. PCT/IB2019/001105, filed on Oct. 11, 2019.

(60) Provisional application No. 62/744,958, filed on Oct. 12, 2018.

(51) Int. Cl.
| | |
|---|---|
| A61K 31/496 | (2006.01) |
| A61K 45/06 | (2006.01) |
| A61P 5/28 | (2006.01) |
| A61P 5/38 | (2006.01) |

(52) U.S. Cl.
CPC ............ *A61K 31/496* (2013.01); *A61K 45/06* (2013.01); *A61P 5/28* (2018.01); *A61P 5/38* (2018.01)

(58) Field of Classification Search
None
See application file for complete search history.

(56) References Cited

U.S. PATENT DOCUMENTS

2010/0280046 A1    11/2010    Stewart

FOREIGN PATENT DOCUMENTS

WO    2006072881 A1    7/2006

OTHER PUBLICATIONS

Auchus et al., "2S,4R-Ketoconazole Is The Relevant Enantiomer Of Ketoconazole For Cortisol Synthesis Inhibition: Steroidogenic P450s Inhibition Involves Multiple Mechanisms", 2018, Endocrine Society, Presented Abstract (Year: 2018).*
Barbot et al., "Metabolic syndrome and cardiovascular morbidity in patients with congenital adrenal hyperplasia", 2022, Frontiers in Endocrinology, 13, pp. 01-10 (Year: 2022).*
Campbell et al., "Metformin: a new oral biguanide", 1996, Clinical Therapeutics, 18, pp. 360-371 (Year: 1996).*
Mapas-Dimaya et al., "Metformin-responsive classic salt-losing congenital adrenal hyperplasia due to 21-hydroxylase deficiency: a case report", 2008, Endocrine Practice, 14, Abstract Only (Year: 2008).*
Kashiwagi et al., "Suppression of primary aldosteronism and resistant hypertension by the peroxisome proliferator-activated receptor gamma agonist pioglitazone", 2013, The American Journal of the Medical Sciences, 345, Abstract Only (Year: 2013).*
Rossi et al., "Primary aldosteronism: cardiovascular, renal and metabolic implications", 2008, Trends in Endocrinology and Metabolism, 19, pp. 88-90 (Year: 2008).*
Sonino et al., "Effect of short-term ketoconazole administration in primary aldosteronism", 1988, Medical Science Research, 16, pp. 535-536. (Year: 1988).*
Jacobs et al., "Late-onset congenital adrenal hyperplasia: a treatable cause of anxiety", 1999, Society of Biological Psychiatry, 46, pp. 856-859 (Year: 1999).*
Engelhardt et al., "Ketoconazole blocks cortisol secretion in man by inhibition of adrenal 11 beta-hydroxylase", 1985, Klin Wochenschr, 63, Abstract (Year: 1985).*
International Search Report and Written Opinion dated Feb. 19, 2020 for PCT/IB2019/001105.
Sonino et al., "Effect of short-term ketoconazole administration in primaryaldosteronism" Medical Science Research, Elsevier Applied Science, Barking, GB, vol. 16, No. 10, Jan. 1, 1988, pp. 535-536.
Aguilar et al., "Treatment of primary, hyperaldosteronism with ketoconazole" Presse Medical, Paris, FR, vol. 20, No. 30, Sep. 28, 1991, p. 1456.
Loechner et al. "Alternative Strategies for the Treatment of Classical Congenital Adrenal Hyperplasia: Pitfalls and Promises", International Journal of Pediatric Endocrinology, Biomed Central Ltd., London, UK, vol. 2010, No. 1, Jun. 8, 2010, p. 670960.
Aguilar Diosdado, M. et al., "Traitement de l'hyperaldostéronisme primaire par le kétoconazole—[Treatment of primary hyperaldosteronism with ketoconazole]," Presse Medicale, 20(30):1456, Elsevier, France, XP009518512 (1991).

\* cited by examiner

Primary Examiner — Mark L Shibuya
Assistant Examiner — Madeline E Braun
(74) Attorney, Agent, or Firm — Sterne, Kessler, Goldstein & Fox P.L.L.C.

(57) ABSTRACT

Disclosed are methods for treating congenital adrenal hyperplasia or primary aldosteronism in a subject in need thereof, comprising administering a therapeutically effective amount of 2S,4R ketoconazole enantiomer substantially free of the 2R,4S ketoconazole enantiomer to the subject. Also disclosed are compositions comprising a therapeutically effective amount of 2S,4R ketoconazole enantiomer substantially free of the 2R,4S ketoconazole enantiomer for use in treating a disease or condition associated with congenital adrenal hyperplasia or primary aldosteronism.

16 Claims, 8 Drawing Sheets

LEVOKETOCONAZOLE FOR TREATMENT OF CONGENITAL ADRENAL HYPERPLASIA AND PRIMARY ALDOSTERONISM

PRIORITY

This application is a continuation of International Patent Application No. PCT/IB2019/001105 filed Oct. 11, 2019 and claims the benefit of U.S. Provisional Patent Application Ser. No. 62/744,958 filed on Oct. 12, 2018 under 35 U.S.C. § 119, the entire disclosure of each are incorporated herein by reference.

FIELD OF THE INVENTION

This invention relates to methods and compositions for treating congenital adrenal hyperplasia or primary aldosteronism in a subject in need thereof, comprising use of a therapeutically effective amount of 2S,4R ketoconazole enantiomer substantially free of the 2R,4S ketoconazole enantiomer.

BACKGROUND OF THE INVENTION

Ketoconazole is a 50/50 racemic mixture of two enantiomers (2S,4R and 2R,4S). Levoketoconazole (COR-003), the single 2S,4R enantiomer of ketoconazole, is a purified form of racemic ketoconazole.

The chemical name of levoketoconazole is 2S,4R cis-1-acetyl-4-[4-[[2-(2,4-dichlorophenyl)-2-(1H-imidazol-1-ylmethyl)-1,3-dioxolan-4-yl]methoxyl]phenyl]piperazine, the formula is $C_{26}H_{28}Cl_2N_4O_4$, and the molecular weight is 531.44. The CAS number is 65277-42-1, and the structural formula is provided below. The chiral centers are at the carbon atoms 2 and 4 as indicated by the arrows.

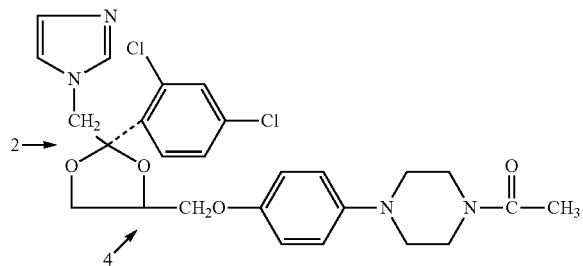

Racemic ketoconazole (the mixture of the two enantiomers 2S,4R and 2R,4S) is an approved drug (NIZORAL®) for the treatment of a variety of fungal infections. Racemic ketoconazole is also used as steroid synthesis inhibitor for medical treatment of Cushing's syndrome (CS).

Congenital adrenal hyperplasia, also called CAH, is a group of genetic disorders in which the two adrenal glands do not work properly. CAH can be severe (classic) and diagnosed in the newborn, but it can also be mild (nonclassic) and not show up until later childhood, adolescence or adulthood. A specific form of CAH is known as l-hydroxylase deficiency. In subjects with CAH due to 11-beta-hydroxylase deficiency, the adrenal glands produce excess androgens, which are male sex hormones, such as aldosterone.

Primary aldosteronism is a hormonal disorder that leads to high blood pressure. It occurs when a subject's adrenal glands produce too much aldosterone. Usually, aldosterone balances sodium and potassium in your blood. But too much of this hormone can cause a patient to lose potassium and retain sodium. That imbalance can cause the patient's body to hold too much water, increasing blood volume and blood pressure.

11-Deoxycorticosterone, or simply deoxycorticosterone, also known as 21-hydroxyprogesterone, desoxycortone, deoxycortone, and cortexone, is a steroid hormone produced by the adrenal gland that possesses mineralocorticoid activity and acts as a precursor to aldosterone. Because 11-deoxycortisol (11-DOC) accumulation is a cardinal finding in 11-hydroxylase deficient CAH, a drug that treats androgen excess in this form of CAH without exacerbating the underlying (pre-existing) 11-DOC burden could be a useful treatment. Similar considerations would also be useful in treating primary aldosteronism.

There are currently few effective treatments for CAH or primary aldosteronism. Accordingly, there is a need for potent steroid synthesis inhibitors useful for treating congenital adrenal hyperplasia or primary aldosteronism, for example by limiting production of aldosterone or its precursor 11-deoxycorticosterone.

SUMMARY OF THE INVENTION

This invention provides a method for treating congenital adrenal hyperplasia in a subject in need thereof, comprising administering a therapeutically effective amount of 2S,4R ketoconazole enantiomer substantially free of the 2R,4S ketoconazole enantiomer to said subject.

This invention also provides a method for treating primary aldosteronism in a subject in need thereof, comprising administering a therapeutically effective amount of 2S,4R ketoconazole enantiomer substantially free of the 2R,4S ketoconazole enantiomer to said subject.

This invention also provides a composition containing a therapeutically effective amount of the 2S,4R ketoconazole enantiomer substantially free of the 2R,4S ketoconazole enantiomer for use in a method of treating, delaying the onset of, or reducing the risk of developing a disease or condition associated with congenital adrenal hyperplasia or primary aldosteronism.

DETAILED DESCRIPTION OF THE INVENTION

Figure 1A:
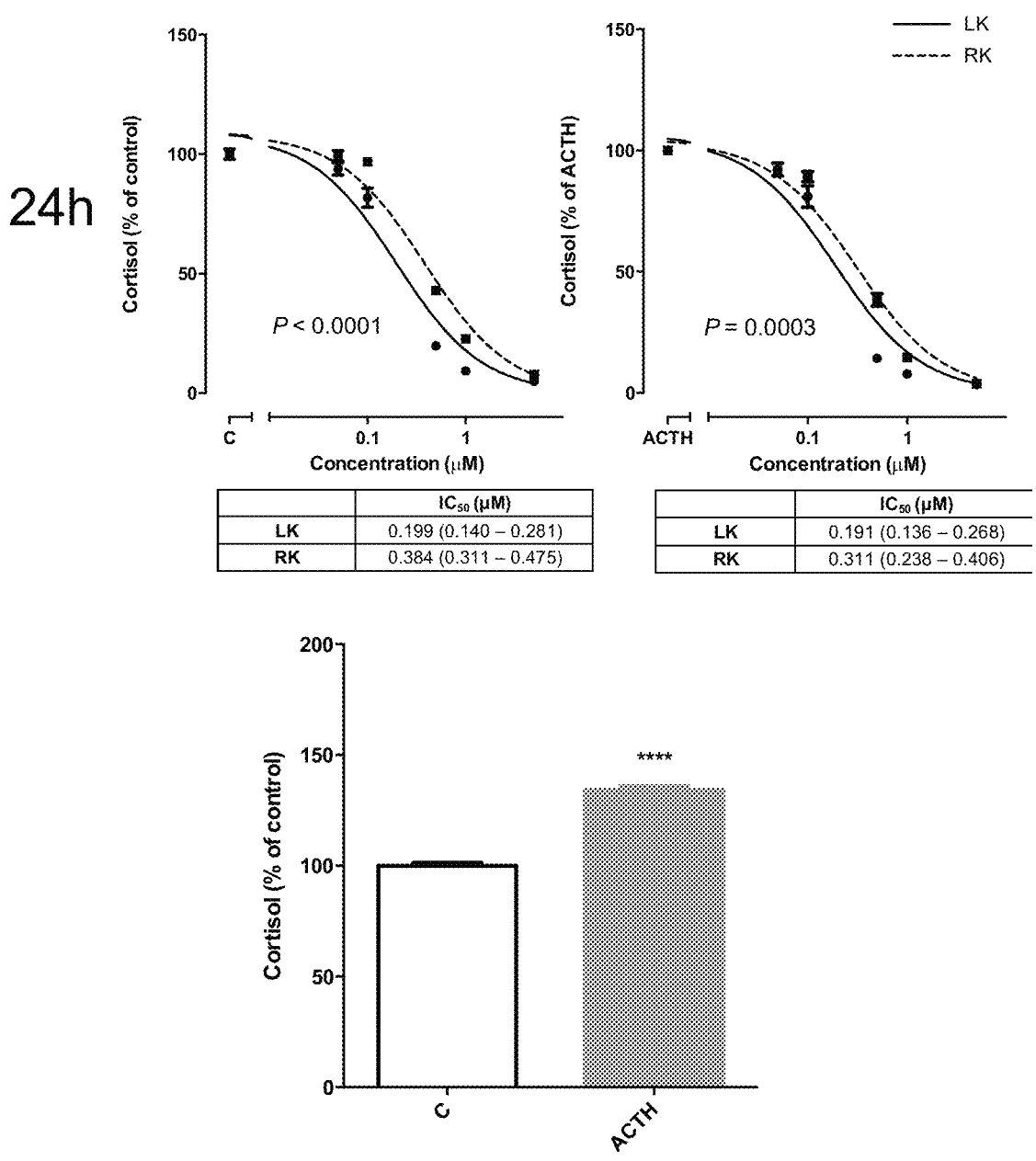
FIGS. 1A and 1B depict dose-dependent effects of levoketoconazole and racemic ketoconazole on cortisol production by HAC15 cells in the basal condition and when stimulated with 10 nM ACTH after 24 hours and 72 hours of incubation, respectively.

All references cited herein are incorporated herein by reference.

The present invention provides pharmaceutical compositions comprising the 2S,4R ketoconazole enantiomer substantially or entirely free of the 2R,4S enantiomer, and methods of using such compositions. Substantially free of the 2R,4S enantiomer, in one embodiment, means that the ketoconazole content of the pharmaceutical composition is less than 2% of the 2R,4S enantiomer and more than 98% of the 2S,4R enantiomer. In another embodiment, substantially free of the 2R,4S enantiomer means the ketoconazole content of the pharmaceutical composition is less than 10% of the 2R,4S enantiomer and more than 90% of the 2S,4R enantiomer. In another embodiment, substantially free of the 2R,4S enantiomer means that the ketoconazole content of the pharmaceutical composition is less than 20% of the 2R,4S enantiomer and more than 80% of the 2S,4R enantiomer. The present invention also provides methods for treating diseases and conditions associated with congenital adrenal hyperplasia or primary aldosteronism with these pharmaceutical compositions.

As used herein, the term "not substantially increased" in connection with administration of a therapeutically effective dose of 2S,4R ketoconazole enantiomer to a subject means that the amount of a substance increases less than 10%, or less than 5% or less than 1% compared to the level of the substance in the subject prior to administration of 2S,4R ketoconazole enantiomer.

As used herein, "treating, delaying the onset of, or reducing the risk of developing a disease or condition" includes ameliorating, mitigating or preventing the occurrence of one or more symptoms associated with the disease or condition.

The invention includes the following embodiments of the methods of the Summary of the Invention above.

The method wherein the ketoconazole content of the therapeutically effective amount comprises less than 20% of the 2R,4S enantiomer and more than 80% of the 2S,4R enantiomer.

The method wherein the ketoconazole content of the therapeutically effective amount comprises less than 10% of the 2R,4S enantiomer and more than 90% of the 2S,4R enantiomer.

The method wherein the ketoconazole content of the therapeutically effective amount comprises less than 2% of the 2R,4S enantiomer and more than 98% of the 2S,4R enantiomer.

The method wherein the ketoconazole content of the therapeutically effective amount comprises less than 1% of the 2R,4S enantiomer and more than 99% of the 2S,4R enantiomer.

The method wherein the congenital adrenal hyperplasia is due to 11-hydroxylase deficiency.

The method wherein the congenital adrenal hyperplasia is of the classic form.

The method wherein 11-DOC secretion is not substantially increased after administration of the 2S,4R ketoconazole enantiomer.

The method of any of claims 1 through 8 wherein the therapeutically effective amount of 2S,4R ketoconazole enantiomer is from about 50 mg to about 600 mg.

The method wherein the therapeutically effective amount of 2S,4R ketoconazole enantiomer is in a pharmaceutical composition comprising a pharmaceutically acceptable carrier.

The method wherein the therapeutically effective amount of 2S,4R ketoconazole enantiomer is co-administered with one or more other active compounds.

The method wherein the one or more active compounds is selected from the group consisting of biguanides, sulfonylureas, HMG-CoA reductase inhibitors, PPAR agonists, PTP-1B inhibitors, DPP-IV inhibitors, and anti-obesity compounds.

The invention includes the following embodiments of the composition of the Summary of the Invention above.

The composition wherein the ketoconazole content of the therapeutically effective amount comprises less than 20% of the 2R,4S enantiomer and more than 80% of the 2S,4R enantiomer.

The composition wherein the ketoconazole content of the therapeutically effective amount comprises less than 10% of the 2R,4S enantiomer and more than 90% of the 2S,4R enantiomer.

The composition wherein the ketoconazole content of the therapeutically effective amount comprises less than 2% of the 2R,4S enantiomer and more than 98% of the 2S,4R enantiomer.

The composition wherein the ketoconazole content of the therapeutically effective amount comprises less than 1% of the 2R,4S enantiomer and more than 99% of the 2S,4R enantiomer.

The composition comprising a pharmaceutically acceptable carrier.

The composition of wherein 11-DOC secretion is not substantially increased when administered to a subject.

The composition wherein the therapeutically effective amount of 2S,4R ketoconazole enantiomer is from about 50 mg to about 600 mg.

The composition wherein the disease or condition is associated with congenital adrenal hyperplasia.

The composition wherein the congenital adrenal hyperplasia is due to 11-hydroxylase deficiency.

The composition wherein the congenital adrenal hyperplasia is of the classic form.

The composition wherein the disease or condition is associated with primary aldosteronism.

The composition further comprising one or more active compounds other than the therapeutically effective amount of 2S,4R ketoconazole enantiomer.

The composition wherein the one or more active compounds is selected from the group consisting of biguanides, sulfonylureas, HMG-CoA reductase inhibitors, PPAR agonists, PTP-1B inhibitors, DPP-IV inhibitors, and anti-obesity compounds.

Embodiments of this invention, including the embodiments above as well as any other embodiments described herein, can be combined in any manner, and the descriptions of variables and components in the embodiments pertain not only to the 2S,4R ketoconazole enantiomer substantially free of the 2R,4S ketoconazole enantiomer but also to a pharmaceutically acceptable salt, hydrate or solvate thereof, or a prodrug or active metabolite thereof. Notably, any of the embodiments above can be further embodied by any other embodiment above, such as wherein any embodiment above can further embody any of the embodiments preceding it. In addition, embodiments of this invention, including the embodiments above as well as any other embodiments described herein, and any combination thereof, pertain to the methods and compositions, including any of the dosage form embodiments described below, of the present invention.

To aid in understanding the invention, this detailed description is organized as follows. Section I describes methods for preparing the 2S,4R enantiomer, its solvates and salts, and pharmaceutical compositions comprising it. Section II describes unit dosage forms of the pharmaceutical compositions of the invention and methods for administering them. Section III describes methods for treating diseases and conditions associated with congenital adrenal hyperplasia or primary aldosteronism by administration of the 2S,4R ketoconazole enantiomer and pharmaceutical compositions comprising the 2S,4R ketoconazole enantiomer substantially free of the 2R,4S enantiomer.

I. Preparation of the 2S,4R Ketoconazole Enantiomer and Pharmaceutical Compositions Containing the 2S,4R Ketoconazole Enantiomer Substantially or Entirely Free of the 2R,4S Ketoconazole Enantiomer As used herein, a composition containing "the 2S,4R ketoconazole enantiomer substantially or entirely free of the 2R,4S ketoconazole enantiomer" includes compositions that do not contain the 2R,4S ketoconazole enantiomer as well as compositions that contain substantially less of the 2R,4S ketoconazole enantiomer, relative to the amount of the 2S,4R enantiomer, than do racemic ketoconazole compositions currently approved for therapeutic use. Compositions useful in the methods of the invention include, for example and without limitation, compositions in which the total ketoconazole content is comprised of at least 80%, or at least 90%, or at least 99%, or at least 99.5%, or at least 99.9% or greater of the 2S,4R enantiomer.

The 2S,4R enantiomer of ketoconazole may be obtained by optical resolution of racemic ketoconazole. Such resolution can be accomplished by any of a number of resolution methods well known to a person skilled in the art, including but not limited to those described in Jacques et al., "Enantiomers, Racemates and Resolutions," Wiley, New York (1981), incorporated herein by reference. For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired enantiomer. Yet another method for obtaining compositions of the 2S,4R enantiomer substantially free of the 2R,4S enantiomer is a fractional crystallization of the diastereomeric salt of ketoconazole with (+)-camphor-10-sulfonic acid.

The 2S,4R enantiomer of ketoconazole can also be prepared directly by a variety of methods known to those of skill in the art. For example, the 2S,4R enantiomer can be prepared directly by transketolization reactions between 2-bromo-2',4'-dichloroacetophenone and optically pure solketal tosylates, as described by Rotstein et al., *J. Med. Chem.* 1992, 35(15), 2818-25.

The present invention also provides a variety of pharmaceutically acceptable salts of the 2S,4R enantiomer of ketoconazole for use in the pharmaceutical compositions of the invention. The term "pharmaceutically acceptable salt" refers to salts prepared from pharmaceutically acceptable bases or acids, including inorganic or organic bases and inorganic or organic acids. Salts derived from inorganic bases include aluminum, ammonium, calcium, copper, ferric, ferrous, lithium, magnesium, manganic, manganous, potassium, sodium, and zinc salts, and the like. The ammonium, calcium, magnesium, potassium, and sodium salts, in particular, can be preferred for some pharmaceutical formulations. Salts in the solid form can exist in more than one crystal structure and can also be in the form of hydrates and polyhydrates. The solvates, and, in particular, the hydrates of the 2S,4R ketoconazole enantiomer are useful in the preparation of the pharmaceutical compositions of the present invention.

Salts derived from pharmaceutically acceptable organic bases include salts of primary, secondary and tertiary amines, substituted amines, including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine, and the like.

When the compound to be formulated is basic, salts can be prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acid, and the like. Illustrative pharmaceutically acceptable acids include citric, hydrobromic, hydrochloric, maleic, phosphoric, sulfuric, and tartaric acids. Ketoconazole compounds are often basic, because the triazole ring is basic. The 2S,4R ketoconazole compound can be made and handled as a non-pharmaceutically acceptable salt (e.g. trifluoroacetate salts) during synthesis and then converted as described herein to a pharmaceutically acceptable salt.

Suitable pharmaceutically acceptable salts of the 2S,4R ketoconazole enantiomer include, but are not limited to, the mesylate, maleate, fumarate, tartrate, hydrochloride, hydrobromide, esylate, p-toluenesulfonate, benzoate, acetate, phosphate, and sulfate salts. For the preparation of pharmaceutically acceptable acid addition salts of the compound of 2S,4R ketoconazole, the free base can be reacted with the desired acids in the presence of a suitable solvent by conventional methods. Similarly, an acid addition salt can be converted to the free base form by methods known to those of skill in the art.

Pharmaceutical compositions of the invention can include metabolites of the 2S,4R ketoconazole enantiomer that are therapeutically active or prodrugs of the enantiomer. Prodrugs are compounds that are converted to therapeutically active compounds as they are being administered to a patient or after they have been administered to a patient.

Thus, the pharmaceutical compositions of the invention comprise the 2S,4R ketoconazole enantiomer, or a pharmaceutically acceptable salt, hydrate or solvate thereof, or a prodrug or active metabolite thereof, in combination with a pharmaceutically acceptable carrier and substantially or entirely free of the 2R,4S enantiomer. In one embodiment, the pharmaceutical composition contains a therapeutically effective amount of the 2S,4R anantiomer of ketoconazole or a pharmaceutically acceptable salt thereof and a pharmaceutically acceptable carrier. As noted above, pharmaceutically acceptable salts of the 2S,4R enantiomer useful in such compositions include, but are not limited to, the hydrochloride, phosphate, maleate, fumarate, tartrate, mesylate, esylate, and sulfate salts.

The "therapeutically effective amount" of the 2S,4R enantiomer of ketoconazole or pharmaceutically acceptable salt thereof will depend on the condition to be treated, the route and duration of administration, the physical attributes of the patient, including weight and other medications taken concurrently, and may be determined according to methods well known to those skilled in the art in light of the present disclosure (see Section II, below). The pharmaceutical compositions of the invention can be conveniently prepared in unit dosage form by methods well-known in the art of pharmacy as medicaments to be administered orally, parenterally (including subcutaneous, intramuscular, and intravenous administration), ocularly (ophthalmic administration), rectally, pulmonarily (nasal or oral inhalation), topically, transdermally or via buccal transfer.

The pharmaceutical compositions of the invention can be prepared by combining the 2S,4R ketoconazole enantiomer with a selected pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are typically preferred over oral liquid preparations.

Thus, in one embodiment, the pharmaceutically acceptable carrier is a solid and the pharmaceutical composition is a tablet for oral administration. Other suitable forms of the pharmaceutical compositions of the invention for oral administration include compressed or coated pills, dragees, sachets, hard or soft gelatin capsules, sublingual tablets, syrups and suspensions. The oral solid dosage forms may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and/or a sweetening agent such as sucrose, lactose, or saccharin. Capsules may also contain a liquid carrier such as a fatty oil. Various other materials may be present to act as coatings or to modify the physical form of the dosage unit. For instance, tablets may be coated with shellac, sugar or both. Tablets may be coated by standard aqueous or nonaqueous techniques. The typical percentage of active compound in these compositions may, of course, be varied from, for example and without limitation, about 2 percent to about 60 percent on a w/w basis.

In another embodiment, the pharmaceutically acceptable carrier is a liquid, and the pharmaceutical composition is intended for oral administration. Oral liquids suitable for use in such compositions include syrups and elixirs and can contain, in addition to the active ingredient, sucrose as a sweetening agent, methyl and propylparabens as preservatives, a dye, and/or a flavoring, such as cherry or orange flavor.

In another embodiment, the present invention provides a pharmaceutical composition of the 2S,4R ketoconazole enantiomer suitable for parenteral administration. For parenteral administration, the pharmaceutical composition is typically contained in ampules or vials and consists essentially of an aqueous or non-aqueous solution or emulsion. These compositions are typically in the form of a solution or suspension, and are typically prepared with water, and optionally include a surfactant such as hydroxypropylcellulose. Dispersions can be prepared in glycerol, liquid polyethylene glycols, and mixtures thereof in oils. Typically, preparations that are in diluted form also contain a preservative.

In another embodiment, the pharmaceutically acceptable carrier is a liquid, and the pharmaceutical composition is an injectable solution. The pharmaceutical injectable dosage forms, including aqueous solutions and dispersions and powders for the extemporaneous preparation of injectable solutions or dispersions, are also sterile and, at the time of administration, are sufficiently fluid for easy syringeability. These compositions are stable under the conditions of manufacture and storage and are typically preserved. The carrier thus includes the solvent or dispersion medium containing, for example, water, ethanol, polyol (e.g. glycerol, propylene glycol and liquid polyethylene glycol), suitable mixtures thereof, and vegetable oils.

In another embodiment, the pharmaceutically acceptable carrier is a gel, and the pharmaceutical composition is provided in the form of a suppository. For rectal administration, the pharmaceutical composition is provided in a suppository, and the pharmaceutical acceptable carrier is a hydrophilic or hydrophobic vehicle. In another embodiment, the pharmaceutical composition useful in the methods of the invention is prepared for topical application, and the 2S,4R ketoconazole enantiomer is formulated as an ointment. The 2S,4R enantiomer can also be administered transdermally; suitable transdermal delivery systems are known in the art.

The pharmaceutical compositions of the invention also include sustained release compositions. Suitable sustained release compositions include those described in U.S. patent application publication Nos. 2005/0013834; 2003/0190357; and 2002/055512 and PCT patent application publication Nos. WO 03011258 and 0152833, each of which is incorporated herein by reference.

II. Unit Dosage Forms; Frequency and Duration of Administration

As noted above, any suitable route of administration can be employed for providing a mammalian subject with a therapeutically effective dose of the 2S,4R enantiomer. The mammalian subject is typically a human, but mammals of veterinary importance, such as cattle, horses, pigs, sheep, dogs, and cats, can also benefit from the methods described herein. For example, oral, rectal, topical, parenteral, ocular, pulmonary, or nasal administration can be employed. Dosage forms include tablets, troches, dispersions, suspensions, solutions, capsules, creams, ointments, aerosols and the like. In many embodiments of the treatment methods of the invention, the pharmaceutical composition is administered orally. The therapeutically effective dosage of the active ingredient varies depending on the particular compound employed (salt, solvate, prodrug, or metabolite), the mode of administration, the condition being treated, and the severity of the condition. Such dosages may be ascertained readily by a person skilled in the art in light of the disclosure herein.

When treating or preventing the diseases and conditions as described herein, satisfactory results can obtained when the 2S,4R ketoconazole enantiomer is administered at a daily dosage of from about 0.1 to about 25 milligrams (mg) per kilogram (mpk) of body weight, preferably given as a single daily dose or in divided doses about two to six times a day. For oral administration to a human adult patient, the therapeutically effective amount will generally be administered in the range of 50 mg to 800 mg per dose, including but not limited to 100 mg per dose, 200 mg per dose, and 400 mg per dose, and multiple, usually consecutive daily doses will be administered in a course of treatment. The 2S,4R ketoconazole enantiomer pharmaceutical composition can be administered at different times of the day. In one embodiment the optimal therapeutic dose can be administered in the evening. In another embodiment the optimal therapeutic dose can be administered in the morning. The total daily dosage of the 2S,4R ketoconazole enantiomer thus can in one embodiment range from about 10 mg to about 2 g, and often ranges from about 10 mg to about 1 g, and most often ranges from about 100 mg to about 500 mg. In the case of a typical 70 kg adult human, the total daily dose of the 2S,4R ketoconazole enantiomer can range from about 10 mg to about 1000 mgs and will often range, as noted above, from about 50 mg to about 800 mg. This dosage may be adjusted to provide the optimal therapeutic response.

In one embodiment, the unit dosage form is suitable for oral administration and contains one or more pharmaceutical excipients. Examples of pharmacologically inactive excipients that can be included in an orally available formulation of the 2S,4R enantiomer of ketoconazole for purposes of the present invention and their function are provided in the following table.

| Inactive Ingredient | Trade Name | Grade | Function |
|---|---|---|---|
| Silicified Microcrystalline Cellulose | Prosolv HD 90 | NF | Diluent |
| Lactose Monohydrate | Modified, 316 Fast Flo | NF | Diluent |
| Corn Starch | STA-Rx NF | NF | Disintegrant |
| Magnesium Stearate | N/A | NF | Lubricant |
| Colloidal Silicon Dioxide | Cab-O-Sil M5P | NF | Glidant |

The excipients listed in the preceding table can be combined in varying proportion with the 2S,4R enantiomer to obtain specific drug tablet and manufacturing characteristics. The drug tablet size can vary from 1 mg total weight to 1000 mg total weight; for example and without limitation, from 100 mg total weight to 800 mg total weight. The proportion of the 2S,4R enantiomer present in the drug tablet can vary from 1% to 100%; for example and without limitation, from 10% to 90%. An example of a 400 mg tablet with the 2S,4R enantiomer comprising 50% of the tablet weight is provided in the following table. In this example, dry blends were made with the (−) cis 2S,4R ketoconazole and the listed inactive excipients and pressed as a dry blend into tablets.

| Component | % w/w (mg) | Tablet Weight |
|---|---|---|
| (—)cis 2S,4R Ketoconazole | 50.0 | 200 |
| Lactose Monohydrate, NF | 22.4 | 89.6 |
| Silicified Microcrystalline Cellulose, NF | 16.5 | 66.0 |
| Corn Starch, NF | 10.0 | 40.0 |
| Colloidal Silicon Dioxide, NF | 0.5 | 2.0 |
| Magnesium Stearate, NF | 0.6 | 2.4 |
| Total | 100.0 | 400.0 |

A drug tablet formulation for 2S,4R ketoconazole has been described in U.S. Pat. No. 6,040,307. This formulation included the active drug substance, (−)-ketoconazole, lactose, corn starch, water and magnesium sStearate. Wet granules were generated with the ketoconazole, lactose, water and corn starch and these granules were dried in an oven prior to compressing into tablets with magnesium stearate and more corn starch. Tablets were compressed and dried. This is a less optimal method than using a dry blend process wherein excess water and elevated temperatures are not introduced. Ketoconazole can undergo degradation (oxidation) (Farhadi and Maleki (2001). "A new spectrophotometric method for the determination of ketoconazole based on the oxidation reactions." *Analytical Sciences* 17 Supplement, i867-869. The Japan Society for Analytical Chemistry), and oxidation reactions are accelerated in the presence of water and elevated temperatures.

The solid unit dosage forms of the pharmaceutical compositions of the invention contain the 2S,4R ketoconazole enantiomer or a salt or hydrate thereof in an amount ranging from about 1 mg to about 2 g, often from about 1.0 mg to about 1.0 g, and more often from about 10 mg to about 500 mg. In the liquid pharmaceutical compositions of the invention suitable for oral administration, the amount of the 2S,4R ketoconazole enantiomer can range from about 1 mg/ml to about 200 mg/ml. The therapeutically effective amount can also be an amount ranging from about 10 mg/ml to about 100 mg/ml. In one embodiment, the dose of the liquid pharmaceutical composition administered is an amount between 0.5 ml and 5.0 ml. In another embodiment, the dose is between about 1 ml and 3 ml. In the liquid pharmaceutical compositions of the invention designed for intravenous or subcutaneous administration the amount of the 2S,4R ketoconazole the amount of the 2S,4R enantiomer can range from about 0.01 to 1 mg/ml and can be administered at a rate of between 0.01 to 1 ml/minute by either a subcutaneous or intravenous administration. Alternatively the amount of the 2S,4R enantiomer can range from about 0.1 mg/ml to 10 mg/ml and can be administered at a rate of between 0.001 ml/minute to 0.1 ml/minute by either of a subcutaneous or intravenous administration.

An illustrative formulation of the 2S,4R enantiomer of ketoconazole substantially free of the 2R,4S enantiomer (hereinafter called DIO-902) is described herein. Secondary benefits of this drug candidate are expected to include reduced total and LDL cholesterol, reduced blood pressure and reduced visceral adiposity. As racemic ketoconazole also inhibits cortisol synthesis, this drug is used as a non-approved therapy for patients with Cushing's syndrome. In these patients racemic ketoconazole reduces glucose, cholesterol, and blood pressure. As cortisol may be a contributing causal factor in the development of type 2 diabetes, clinical trials with racemic ketoconazole have been carried out in these patients. The results of these clinical trials support treating type 2 diabetes through lowering of plasma cortisol. Racemic ketoconazole has, however, been associated with hepatotoxicity. Preclinical results support that DIO-902 may be safer and more efficacious than the racemic mixture.

DIO-902 comprises the 2S,4R enantiomer of ketoconazole (2S,4R cis-1-acetyl-4-[4-[[2-(2,4-dichlorophenyl)-2-(1H-imidazol-1-ylmethyl)-1,3-dioxolan-4-yl]methoxy]phenyl]piperazine), purified from racemic ketoconazole and is largely (greater than 99%) free of the 2R,4S enantiomer. DIO-902 is an immediate release 200 mg strength tablet to be taken orally and formulated using cellulose, lactose, cornstarch, colloidal silicon dioxide and magnesium stearate as shown in the table below.

| Component | Trade Name | Percentage |
|---|---|---|
| 2S,4R-ketoconazole | | 50 |
| Silicified Microcrystalline Cellulose, NF | Prosolv HD 90 | 16.5 |
| Lactose Monohydrate, NF | 316 Fast Flo | 22.4 |

-continued

| Component | Trade Name | Percentage |
|---|---|---|
| Corn Starch, NF | STA-Rx NF | 10 |
| Magnesium Stearate, NF | N/A | 0.6 |
| Colloidal Silicon Dioxide, NF | Cab-O-Sil M5P | 0.5 |

The drug product may be stored at room temperature and is anticipated to be stable for at least 2 years at 25° C. and 50% RH. The drug is packaged in blister packs.

Additional characterization of the physical, chemical and pharmaceutical properties of DIO 902 are described in U.S. Pat. No. 9,918,984, incorporated herein by reference.

As noted above, the pharmaceutical compositions of the invention will typically be administered for multiple consecutive days for periods ranging from one or more weeks to one, several, or many months (e.g., at least 7, 14, 28, 60 or 120 days). In one embodiment, the pharmaceutical compositions of the invention are administered for the treatment of a chronic disease, condition, or indication for treatment periods ranging from one month to twelve months. In another embodiment, the 2S,4R enantiomer is administered from one year to five years. In another embodiment, the 2S,4R enantiomer is administered from 5 years to 20 years. In another embodiment, the 2S,4R enantiomer is administered until there is remission from the disease or for the life of the patient.

The duration of administration in accordance with the methods of the invention depends on the disease or condition to be treated, the extent to which administration of the pharmaceutical composition has ameliorated the disease symptoms and conditions, and the individual patient's reaction to the treatment.

III. Treating Diseases and Conditions Associated with Congenital Adrenal Hyperplasia or Primary Aldosteronism Using Pharmaceutical Compositions of the Invention In view of the foregoing, this invention provides methods and compositions for using the 2S,4R enantiomer of ketoconazole for the treatment, control, amelioration, prevention, delay in the onset of or reduction of the risk of developing the diseases and conditions due to congenital adrenal hyperplasia or primary aldosteronism in a mammalian patient, particularly a human. In one embodiment, the method involves the administration of a therapeutically effective amount of the 2S,4R ketoconazole enantiomer or a pharmaceutically acceptable salt or solvate thereof, substantially or entirely free of other ketoconazole enantiomers, to the patient suffering from the disease or condition.

This invention provides methods for treating a disease or condition associated with congenital adrenal hyperplasia or primary aldosteronism in a mammalian patient in need of such treatment, said methods comprising administering to the patient a therapeutically effective amount of a pharmaceutical composition of the 2S,4R ketoconazole enantiomer substantially free of the 2R,4S enantiomer.

In another aspect, the present invention provides a method of delaying the onset of a condition associated with congenital adrenal hyperplasia or primary aldosteronism in a mammalian patient in need of such treatment, said method comprising administering to the patient a therapeutically effective amount of a pharmaceutical composition of the 2S,4R ketoconazole enantiomer substantially free of the 2R,4S enantiomer.

In another aspect, the present invention provides a method of reducing the risk of developing a condition associated with congenital adrenal hyperplasia or primary aldosteronism a mammalian patient in need of such treatment, said method comprising administering to the patient a therapeutically effective amount of a pharmaceutical composition of the 2S,4R ketoconazole enantiomer substantially free of the 2R,4S enantiomer.

Notably, the invention provides a method for treating a disease or condition associated with congenital adrenal hyperplasia or primary aldosteronism in a subject not diagnosed with or under treatment for a fungal infection, by administering a pharmaceutical composition comprising a pharmaceutically acceptable carrier and a therapeutically effective amount of 2S,4R ketoconazole enantiomer substantially free of the 2R,4S ketoconazole enantiomer to the subject.

In certain aspects of the invention, a patient being treated with a pharmaceutical composition of the 2S,4R ketoconazole enantiomer substantially free of the 2R,4S enantiomer is not diagnosed with and/or is not under treatment for one or more diseases, disorders, or conditions independently selected from the following: (1) hyperglycemia, (2) low glucose tolerance, (3) insulin resistance, (4) obesity, (5) a lipid disorder, (6) dyslipidemia, (7) hyperlipidemia, (8) hypertriglyceridemia, (9) hypercholesterolemia, (10) low HDL levels, (11) high LDL levels, (12) atherosclerosis (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) prostate cancer, (22) benign prostatic hyperplasia, (23) fungal infection and (24) other conditions and disorders where insulin resistance is a component.

Congenital adrenal hyperplasia, also called CAH, is a group of genetic disorders in which the two adrenal glands do not work properly. People inherit one gene that causes this disorder from each of their parents. This is known as a recessive genetic disorder. This means that carriers of the trait show no symptoms, but when one has a double dose of the trait, problems occur. The reason for these problems is that the adrenal glands, located on top of each kidney, cannot efficiently produce the hormones that are essential for body functions.

Some subjects with CAH lack one of the enzymes (proteins that cause chemical changes in the body), steroid 21-hydroxylase. This results in low production of the hormone (cortisol) that helps the body respond to stress, and in most cases of classic CAH they lack another hormone (aldosterone) needed to retain sodium. Individuals affected by classic CAH caused by 21-hydroxylase deficiency produce excess adrenal steroids that lead to the production of testosterone and related male-like hormones. CAH can be severe (classic) and diagnosed in the newborn, but it can also be mild (nonclassic) and not show up until later childhood, adolescence or adulthood.

A specific form of CAH is known as 11-hydroxylase deficiency. Congenital adrenal hyperplasia (CAH) due to 11-beta-hydroxylase deficiency is one of a group of disorders (collectively called congenital adrenal hyperplasia) that affect the adrenal glands. In subjects with CAH due to 1-beta-hydroxylase deficiency, the adrenal glands produce excess androgens, which are male sex hormones. Females with the classic form of CAH due to 11-beta-hydroxylase deficiency have external genitalia that do not look clearly male or female (atypical genitalia). However, the internal reproductive organs develop normally. Males and females with the classic form of this condition have early development of their secondary sexual characteristics such as growth of facial and pubic hair, deepening of the voice, appearance of acne, and onset of a growth spurt. The early growth spurt can prevent growth later in adolescence and lead to short stature in adulthood. In addition, approximately two-thirds of individuals with the classic form of CAH due to 11-beta-hydroxylase deficiency have high blood pressure that typically develops within the first year of life. Females with the non-classic form of CAH due to 11-beta-hydroxylase deficiency have normal female genitalia. As affected females get older, they may develop excessive body hair growth (hirsutism) and irregular menstruation. Males with the non-classic form of this condition do not typically have any signs or symptoms except for short stature. Hypertension is not a feature of the non-classic form of CAH due to 11-beta-hydroxylase deficiency.

We have surprisingly found that levoketoconazole has less propensity to increase 11-deoxycorticosterone secretion from human adrenal cells in the presence of adrenocorticotropic hormone (ACTH) drive compared to racemic ketoconazole. DOC is a precursor to aldosterone. Increased aldosterone (as a result of increased DOC) would be unfavorable to CAH therapy. Because 11-DOC accumulation is a cardinal finding in 11-hydroxylase deficient CAH, a drug that treats androgen excess in this form of CAH without exacerbating the underlying (pre-existing) 11-DOC burden could be a useful treatment. Such a treatment would potentially allow for reduced cortisol replacement requirements to normalize ACTH and thus reduce corticosteroid-related side effects (collectively known as exogenous CS). Levoketoconazole would tend to induce less adverse effects relating to pre-existing high blood pressure at any given therapeutic level compared to racemic ketoconazole.

Primary aldosteronism is a hormonal disorder that leads to high blood pressure. It occurs when a subject's adrenal glands produce too much aldosterone. Usually, aldosterone balances sodium and potassium in your blood. But too much of this hormone can cause a patient to lose potassium and retain sodium. That imbalance can cause the patient's body to hold too much water, increasing blood volume and blood pressure.

Notably, racemic ketoconazole has been demonstrated to accumulate in a subject's body over repeated dosing, leading to adverse effects such as hepatotoxicity. In contrast, levoketoconazole has significantly less accumulation. Treatment of congenital adrenal hyperplasia or primary aldosteronism can be envisioned without significant drug accumulation in the subject to which the 2S,4R ketoconazole enantiomer is administered.

In one embodiment, the 2S,4R is administered over a period of at least 14 days (e.g., 14 days), and preferably at least 28 days (e.g., 28 days). In one embodiment, the doses of 2S,4R enantiomer are administered daily (as a single or multiple daily administration). In one embodiment, the doses of 2S,4R enantiomer are administered on alternate days. In one embodiment, the doses of 2S,4R enantiomer are administered according to another schedule as part of a course of therapy, where the course of therapy lasts at least 28 days and where administration of an equal weight amount (or, alternatively, a double weight amount) of racemic ketoconazole results in accumulation of the drug in the subject.

Accumulation of drug, or the absence of accumulation, can be measured by determining the plasma level of drug on a first day and on a measuring the plasma level of the drug on one or more subsequent days. For example, if the plasma level is measured on a first day, denoted Day 1, subsequent measurements can be made on Day 7 and/or Day 14 and/or Day 28, or daily for 1, 2 or 4 weeks. In one embodiment, determining the plasma level involves measuring a 12 hour or 24 hour AUC. In one embodiment, the cortisol plasma level on Day 1 and on at least one subsequent day selected from Day 7, Day 14 and Day 28 differs by less than about 50%, preferably by less than about 25%, and sometimes by less than 15%. It will be appreciated that, guided by this disclosure, a constant exposure of a particular subject to 1-acetyl-4-[4-[[2-(2,4-dichlorophenyl)-2-[(1H-imidazol-1-yl)-methyl]-1,3-dioxolan-4-yl]methoxy]phenyl]piperazine can also be deduced from administration of doses shown in pharmacokinetic studies to result in constant exposure in a statistically significant number of similar subjects.

In a preferred embodiment, the constant exposure is provided by administering a constant total periodic dose of the 2S,4R enantiomer substantially free of the 2R,4S enantiomer, such as a constant total daily dose (in one or more administrations per day). In an embodiment, the subject has not previously been treated with racemic or enantiomeric ketoconazole. In one embodiment, the subject has not been administered drug for at least 14 days, at least 28 days, or at least 6 months prior to Day 1. In one embodiment the subject is a human patient. In another embodiment, the subject is a dog or is a Sprague-Dawley rat. In an embodiment, the subject is diagnosed with a condition characterized by elevated cortisol levels.

Thus, the present invention provides for a method of co-administering drugs that are commonly co-administered with racemic ketoconazole without the risks of aberrant pharmacokinetics of the co-administered drug or racemic ketoconazole attendant to the administration of racemic ketoconazole.

The pharmaceutical compositions of the invention can be co-administered or otherwise used in combination with one or more other drugs in the treatment, prevention, suppression, or amelioration of the diseases, disorders, and conditions described herein as susceptible to therapeutic intervention in accordance with the methods of the invention. Typically, the combination of the drugs provided by the methods of the present invention is safer or more effective than either drug alone or of the non-2S,4R ketoconazole enantiomer drug in combination with racemic ketoconazole, or the combination is safer or more effective than would be expected based on the additive properties of the individual drugs. Such other drug(s) may be administered by a route and in an amount commonly used contemporaneously or sequentially with a pharmaceutical composition of the 2S,4R ketoconazole enantiomer substantially free of the 2R,4S enantiomer. When a pharmaceutical composition of the 2S,4R ketoconazole enantiomer substantially free of the 2R,4S enantiomer is used contemporaneously with one or more other drugs, a combination product containing such other drug(s) and the 2S,4R ketoconazole enantiomer can be utilized if the two active drugs can be coformulated. Combination therapy in accordance with the methods of the invention also includes therapies in which the pharmaceutical compositions useful in the methods of the invention and one or more other drugs are administered on different overlapping schedules. It is contemplated that, when used in combination with other active ingredients, the pharmaceutical compositions useful in the methods of the present invention or the other active ingredient or both may be used effectively in lower doses than when each is used alone. Accordingly, the pharmaceutical compositions useful in the methods of the present invention include those that contain one or more other active ingredients, in addition to the 2S,4R ketoconazole enantiomer.

Examples of other drugs that may be administered in combination with a pharmaceutical composition of the present invention, either separately or, in some instances, the same pharmaceutical composition, include, but are not limited to:

(a) dipeptidyl peptidase IV (DPP-IV) inhibitors; (b) insulin sensitizers including (i) PPARγ agonists such as the glitazones (e.g. pioglitazone, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin; (c) insulin, insulin analogs, or insulin mimetics; (d) sulfonylureas and other insulin secretagogues such as tolbutamide, glipizide, glyburide, meglitinide, and related materials; (e) α-glucosidase inhibitors (such as acarbose); (f) glucagon receptor antagonists such as those disclosed in PCT patent application publication Nos. WO 98/04528, WO 99/01423, WO 00/39088, and WO 00/69810, each of which is incorporated herein by reference; (g) GLP-1, GLP-1 analogs and mimetics, and GLP-1 receptor agonists such as those disclosed in PCT patent application publication Nos. WO 00/42026 and WO 00/59887, each of which is incorporated herein by reference; (h) GIP, GIP analogs and mimetics, including but not limited to those disclosed in PCT patent application publication No. WO 00/58360, incorporated herein by reference, and GIP receptor agonists; (i) PACAP, PACAP analogs and mimetics, and PACAP receptor 3 agonists such as those disclosed in PCT patent application publication No. WO 01/23420, incorporated herein by reference; (j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as for example ezetimibe and β-sitosterol, (v) acyl CoA:cholesterol acyltransferase inhibitors, such as for example avasimibe, and (vi) anti-oxidants such as probucol; (k) PPARδ agonists, such as those disclosed in PCT patent application publication No. WO 97/28149, incorporated herein by reference; (l) antiobesity compounds such as fenfluramine, dexfenfluramine, phentermine, sibutramine, orlistat, neuropeptide Y5 inhibitors, CB1 receptor inverse agonists and antagonists, and O3 adrenergic receptor agonists; (m) an ileal bile acid transporter inhibitor; (n) agents intended for use in inflammatory conditions other than glucocorticoids, such as aspirin, non-steroidal anti-inflammatory drugs, azulfidine, and cyclooxygenase 2 selective inhibitors, and (o) protein tyrosine phosphatase-1B (PTP-1B) inhibitors.

Thus, in one embodiment, the present invention provides a pharmaceutical composition for use in a method of treating, delaying the onset of, or reducing the risk of developing a disease or condition associated with congenital adrenal hyperplasia or primary aldosteronism that comprises: (1) a therapeutically effective amount of 2S,4R ketoconazole enantiomer substantially free of 2R,4S ketoconazole enantiomer; (2) a therapeutically effective amount of compound selected from the group consisting of: (a) DPP-IV inhibitors; (b) insulin sensitizers selected from the group consisting of (i) PPAR agonists and (ii) biguanides; (c) insulin and insulin analogs and mimetics; (d) sulfonylureas and other insulin secretagogues; (e) α-glucosidase inhibitors; (f) glucagon receptor antagonists; (g) GLP-1, GLP-1 analogs and mimetics, and GLP-1 receptor agonists; (h) GIP, GIP analogs and mimetics, and GIP receptor agonists; (i) PACAP, PACAP analogs and mimetics, and PACAP receptor 3 agonists; (j) cholesterol lowering agents selected from the group consisting of: (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants; (k) PPARδ agonists; (l) antiobesity compounds; (m) an ileal bile acid transporter inhibitor, (n) anti-inflammatory agents other than glucocorticoids; and (o) protein tyrosine phosphatase-1B (PTP-1B) inhibitors; and (3) a pharmaceutically acceptable carrier.

The above pharmaceutical compositions and combination therapies include those in which the 2S,4R ketoconazole enantiomer substantially or entirely free of the 2R,4S enantiomer, or a pharmaceutically acceptable salt, hydrate, or solvate thereof; is coformulated or co-administered with one or more other active compounds. Non-limiting examples include combinations of the 2S,4R ketoconazole enantiomer with two or more active compounds selected from biguanides, sulfonylureas, HMG-CoA reductase inhibitors, PPAR agonists, PTP-1B inhibitors, DPP-IV inhibitors, and antiobesity compounds.

The present study compares the direct effects of levoketoconazole on basal and ACTH-stimulated adrenocortical steroid production to those of racemic ketoconazole. In vitro studies were performed in HAC15 cells and in primary adrenocortical cultures by assessing the concentrations of steroids in the supernatant after treatment with both compounds. Finally, we assessed the pituitary-directed effects of both levoketoconazole and racemic ketoconazole on cell amount and ACTH secretion in corticotroph pituitary cells.

Materials and Methods

Cell Culture and Compounds

Human adrenocortical carcinoma HAC15 and mouse corticotroph AtT20 cells were used, purchased as a kind gift by Dr. W. Rainey, and obtained from Dr. J. Tooze (European Organization for Molecular Biology), respectively. Both cell lines were cultured in 75 cm$^2$ flasks at 37° C. in a humidified incubator (Greiner Bio-One, Alphen a/d Rijn, the Netherlands) at 5% CO$_2$. Dulbecco's Modified Eagle Medium F12 containing 5% fetal calf serum was used for HAC15, whereas AtT20 cells were cultured in Dulbecco's minimal essential medium (DMEM) supplemented with 10% fetal calf serum. Both mediums were supplemented with L-glutamine (2 mmol/L) and penicillin (10$^5$ U/L). Short tandem repeat (str) profiling using a Powerplex Kit (Promega, Leiden, the Netherlands) of HAC15 and AtT20 gave results consistent with the ATCC database, confirming the identity of both cell lines. Medium and supplements were obtained from Invitrogen, Breda, the Netherlands. Once a week, cells were harvested with trypsin (0.05%)-EDTA (0.53 mM) and resuspended in culture medium. Levoketoconazole (COR-003) and racemic ketoconazole (both from Cortendo AB) were dissolved in absolute ethanol (EtOH), according to manufacturer's instructions, and stored at −20° C. at a stock concentration of 10$^{-2}$ μM. At the start of each experiment, both drugs were freshly prepared and diluted in EtOH in the correct concentrations. Synacten (synthetic ACTH, Novartis Pharma A.G.) stock concentration was stored at 4° C. and dissolved in culture medium at the day of use. The final concentrations of ACTH were chosen based on a dose-response curve in HAC15 cells and previously reported studies in the literature. For HAC15, 200,000 and 100,000 cells were plated in 0.5 ml medium in 24 well plates for experiments of 1 and 3 days, respectively. For AtT20, cell amounts were 100,000 and 30,000. One day after seeding the HAC15 cells, the medium was refreshed and cells were treated 1 or 3 days in quadruplicate with levoketoconazole or racemic ketoconazole (0.05-5 µM), with or without 10 nM ACTH. To study effects of both compounds on pituitary AtT20 cells, concentrations of 0.1 to 10 µM of both drugs were used. Controls were vehicle treated. In case the compounds had an effect on cell number, steroid levels were corrected for total amount of DNA per well as a measure of cell number. Media were collected after 1 or 3 days of incubation and stored at −20° C. until analysis. All cell culture experiments were carried out at least twice.

Processing of Human Tissues

To obtain primary cultures, adrenal specimens (adrenocortical adenomas, adrenal hyperplasias and adrenocortical carcinomas) were collected after adrenalectomy at the department of Surgery, Erasmus University Medical Center, Rotterdam, the Netherlands, between April 2016 and May 2018. The study was conducted under guidelines that have been approved by the Medical Ethics Committee of the Erasmus Medical Center and informed consent was obtained from all patients. Immediately after surgery, specimens were minced into small pieces of 2-3 mm$^3$, washed in culture medium and centrifuged for 5 minutes at 600 g. The tissue was stored overnight in culture medium at 4° C., where after the tissue was centrifuged again and the supernatant was removed. Fragments were dissociated using 10-25 ml collagenase type 1 (2 mg/ml: Sigma-Aldrich), followed by incubation at 37° C. for up to two hours. Ficoll (GE healthcare) density gradient separation was used once or twice as required in order to separate contaminating red blood cells from the tumor cells. Cell viability and cell amount were counted by trypan blue exclusion. Dissociated cells were plated at a density of $10^5$ cells per well. ACTH-secreting corticotroph pituitary adenoma tissue from patients with Cushing's disease (n=2) was available after transsphenoidal surgery. Single-cell suspensions of the pituitary adenoma tissues were prepared as previously described in detail.

Primary culture conditions for primary cultures were similar as described in the section 'cell culture and compounds', but with small adjustments: ACTH was used at a concentration of 85 pM (250 pg/mL), treatment was started 3-4 days after plating of the cells and cells were incubated for 3 days, and; for pituitary primary cultures, levoketoconazole and racemic ketoconazole were only tested at a concentration of 1 µM. Owing to a limited number of cells obtained from the specimens, not all experiments were carried out in every primary culture.

As a measure of cell number, DNA concentrations were determined using the bisbenzimide fluorescent dye (Hoechst 33258, Sigma Aldrich), as previously described.

Measurement of Steroid Hormone Concentrations

Cortisol concentrations were measured in the supernatant using a chemiluminescence immunoassay system (Immulite 2000XPi; Siemens DPC Inc., Los Angeles, Calif., USA). In addition, we carried out multi-steroid analysis by liquid chromatography/mass spectrometry (LC/MS-MS) to accurately quantify androstenedione, corticosterone, cortisol, 11-deoxycortisol, DHEA, DHEAS, progesterone, 17-hydroxyprogesterone, and testosterone. Concentrations that were tested on the LC/MS-MS were closest to 50% inhibition or maximal inhibition of cortisol as determined by the immunoassay. Steroids were quantified with respect to a calibration series, with internal standards. Steroids were quantified on a Xevo TQS LC-MS/MS (Waters Chromatography).

At the end of the AtT20 and primary pituitary adenoma culture experiments, medium was collected and supplemented with 1% of the protease inhibitor Trasylol to prevent degradation of ACTH. ACTH was measured using a commercially available, nonisotopic automatic chemiluminescence system (DPC Immulite).

Statistical Analysis

Statistical analysis was performed using Graphpad Prism 6.0 (Graphpad Software, San Diego, CA). Non-linear regression curve fitting program was used to calculate the half maximal inhibitory concentrations ($IC_{50}$) on cortisol production. Effects of both compounds on the steroid profile were measured as absolute change compared to control and compared using the Student's t-test. When assessing differences between effects of both compounds, the percentage change was evaluated and compared in order to correct for differences in the vehicle treated control cells. Values of P<0.05 were considered statistically significant and data are presented as mean SEM.

Results

Figure 1B:
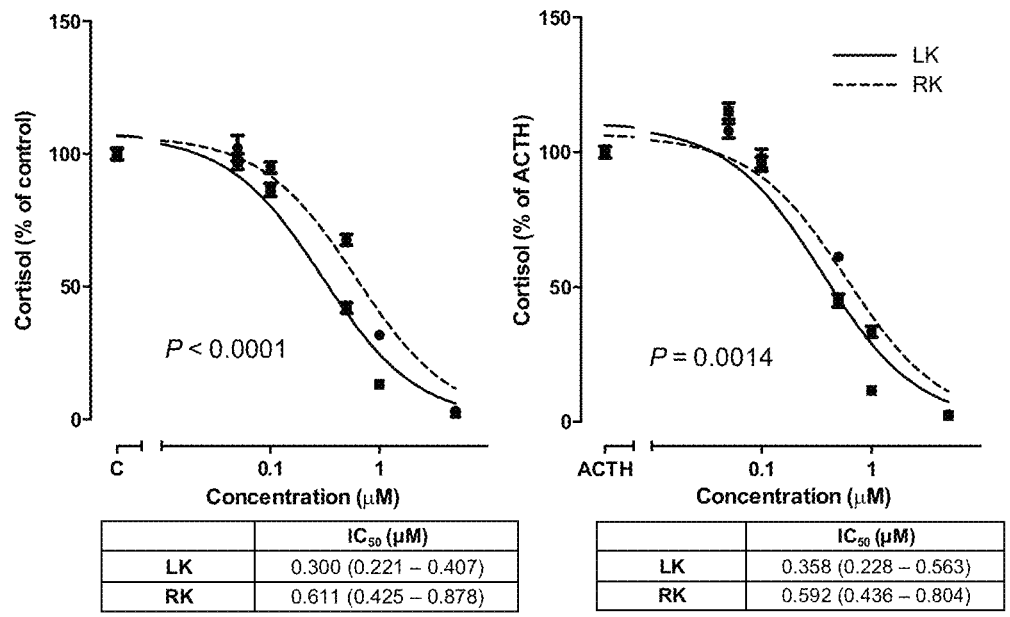
Figure 1B:
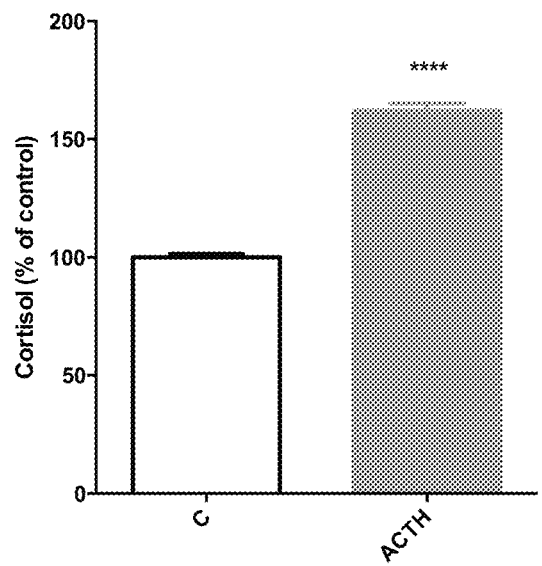

Effects of Racemic Ketoconazole and Levoketoconazole on Cortisol Production In Vitro HAC15 Cells FIGS. 1A and 1B depict dose-dependent effects of levoketoconazole (LK, solid lines) and racemic ketoconazole (RK, dotted lines) on cortisol production by HAC15 cells in the basal condition and when stimulated with 10 nM ACTH after 24 hours (FIG. 1A) and 72 hours (FIG. 1B) of incubation. $IC_{50}$ values are depicted in micromolar amounts with a 95% confidence interval. The P-value in each graph compares the $IC_{50}$ value of levoketoconazole and racemic ketoconazole. Values are depicted as the mean±SEM and as the percentage of vehicle treated control or ACTH stimulated HAC15 cells. **** P<0.0001 versus control. Abbreviations include ACTH, adrenocorticotropic hormone; C, control.

After 3 days of treatment, levoketoconazole more potently suppressed cortisol production in HAC15 cells compared to racemic ketoconazole, with an approximate two-fold lower $IC_{50}$ value (FIG. 1B). Levoketoconazole had an $IC_{50}$ 0.300 µM 95% CI 0.221-0.407 vs. 0.611 µM 95% CI 0.425-0.878, P<0.0001) for racemic ketoconazole. $IC_{50}$ values of both compounds did not significantly change when HAC15 cells were treated for 1 day (FIG. 1A), or were stimulated with ACTH. ACTH stimulation resulted in a mean increase in cortisol of 34% and 61% after 1 and 3 days of incubation, respectively (both showed P<0.0001). In the conditions as mentioned above, no effects were observed on cell number.

Primary Cultures

Characteristics of patients of whom a primary culture was obtained are listed in Table 1, with corresponding numbers that will be used to refer to throughout the Results section. Effects of levoketoconazole and racemic ketoconazole were assessed in 14 primary cultures of human adrenocortical tissue: six cortisol-producing adrenal adenomas (CPA), 2 ectopic ACTH associated adrenal hyperplasia, 3 ACTH-independent adrenal hyperplasia and 3 cortisol-producing ACC. DNA measurement was performed in 28 of 33 primary adrenal culture plates, and showed no effects of the drugs on cell number in these cultures.

Table 1 summarizes the clinical and tumor characteristics of patients of which a primary culture was obtained. Abbreviations used in the table include: ACC, adrenocortical carcinoma; ACTH, adrenocorticotropin hormone; cm, centimeter; EAS, ectopic adrenocorticotropin syndrome; F, female; M, male; yr, years.

TABLE 1

| Patient no | Sex | Site | Age at surgery | Size of lesion (cm) | Weiss score | Steroid production |
|---|---|---|---|---|---|---|
| Cortisol-producing adrenal adenomas | | | | | | |
| No. 1 | F | Left | 57 | 2.5 | 0 | Cortisol |
| No. 2 | F | Left | 67 | 4 | 0 | Cortisol |
| No. 3 | F | Left (Bilateral) | 63 | 4.2 | 0 | Cortisol |
| No. 4 | F | Right | 66 | 3.9 | 0 | Cortisol |
| No. 5 | M | Right | 55 | 6.8 | 2 | Cortisol |
| No. 6 | F | Left | 38 | 3.3 | 0 | Cortisol |

TABLE 1-continued

| Patient no | Sex | Site | Age at surgery | Size of lesion (cm) | Weiss score | Steroid production |
|---|---|---|---|---|---|---|
| EAS associated adrenal hyperplasias | | | | | | |
| No. 1 | F | Bilateral | 79 | — | — | Cortisol |
| No. 2 | F | Left (Bilateral) | 69 | — | — | Cortisol |
| ACTH independent hyperplasias | | | | | | |
| No. 1 | F | Left (Bilateral) | 50 | — | — | Cortisol |
| No. 2 | F | Left | 73 | — | — | Cortisol |
| No. 3 | M | Left | 66 | — | — | Cortisol |
| Adrenocortical carcinoma | | | | | | |
| No. 1 | F | Right | 61 | 5 | 9 | Cortisol |
| No. 2 | M | Left | 64 | 18.5 | 7 | Cortisol |
| No. 3 | F | Right | 67 | 15 | 8 | Cortisol and androgens |

TABLE 2

| Diagnosis | No. | Basal condition Levoketoconazole | Basal condition Racemic ketoconazole | ACTH stimulated cortisol (%) | ACTH simulated condition Levoketoconazole | ACTH simulated condition Racemic ketoconazole |
|---|---|---|---|---|---|---|
| Cortisol-producing adrenal adenomas | 1 | 0.116 (0.0762-0.177) | NT | NT | NT | NT |
| | 2 | 0.125 (0.0809-0.194) | 0.266 (0.158-0.450) # | +145% **** | 0.188 (0.0937-0.378) | NT |
| | 3 | 0.140 (0.0782-0.251) | 0.138 (0.0700-0.274) | +66% **** | 0.187 (0.102-0.342) | 0.241 (0.127-0.460) |
| | 4 | 0.0631 (0.0443-0.0899) | NT | +230 *** | 0.0934 (0.0685-0.127) | 0.0895 (0.0597-0.134) |
| | 5 | NT | NT | +615 **** | NT | 0.204 (0.116-0.360) |
| | 6 | NT | NT | +132% ** | 0.586 (0.272-1.267) | NT |
| EAS associated hyperplasia | 1 | 0.0277 (0.00859-0.0796) | 0.0262 (0.00859-0.122) | +228% **** | 0.0799 (0.0484-0.1321) | 0.1059 (0.0262-0.428) |
| | 2 | 0.0220 (0.00986-0.0492) | 0.0296 (0.00515-0.170) | NT | NT | NT |
| ACTH independent hyperplasia | 1 | Ambiguous | Ambiguous | +34% *** | Ambiguous | Ambiguous |
| | 2 | NT | NT | −14% * | 0.7022 (0.1220-4.041) | 1.394 (0.2770-7.012) |
| | 3 | NT | NT | +2239% **** | 0.117 (0.0763-0.180) | NT |
| ACC | 1 | 0.00578 (0.00270-0.0124) | NT | NT | NT | NT |
| | 2 | 0.0571 (0.0309-0.105) | 0.0763 (0.0430-0.135) | NT | NT | NT |
| | 3 | 0.0731 (0.0477-0.112) | 0.0676 (0.0534-0.0857) | +67% * | 0.0321 (0.0158-0.0651) | NT |

Table 2 summarizes the efficacy of levoketoconazole and racemic ketoconazole on inhibition of cortisol production in human primary adrenocortical cultures. $IC_{50}$ values are presented in micromolar (μM) amounts after 3 days of treatment. ACTH (85 μM) stimulated cortisol represents the mean percentage increase of cortisol production compared to control, with P-value compared to control. "Ambiguous" means that the $IC_{50}$ value could not be calculated, because dose-response curves were not suitable. Abbreviations include: ACC, adrenocortical carcinoma; ACTH, adrenocorticotropin hormone; EAS, ectopic adrenocorticotropin syndrome. * $P<0.05$,  $P<0.01$, and * $P<0.001$, and **** $P<0.0001$ vs vehicle treated control. #$P<0.05$ versus $IC_{50}$ value of levoketoconazole in the same patient. NT, not tested.

Figure 2A:
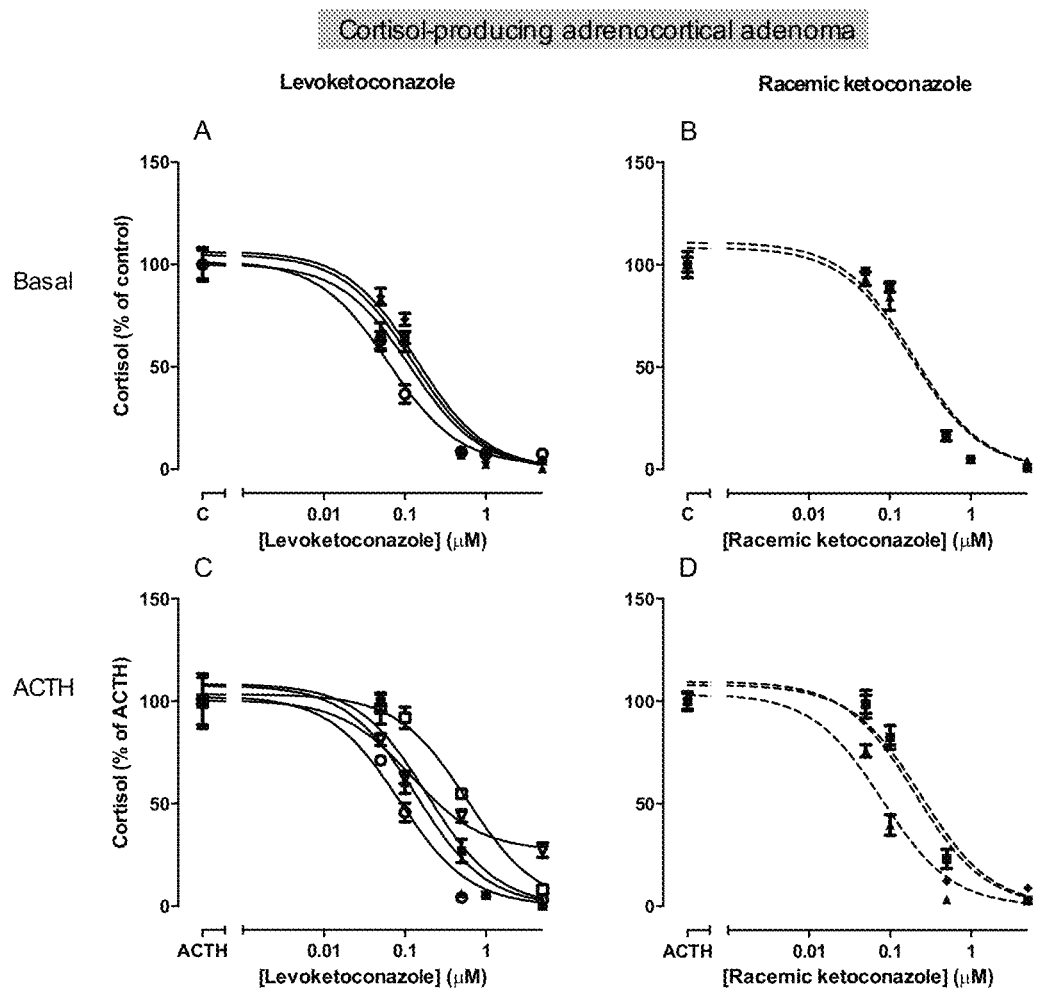
FIG. 2A depicts dose dependent effects of levoketoconazole and racemic ketoconazole on cortisol production in cortisol-producing adrenal adenoma cultures, both ACTH dependent and independent.
Figure 2B:
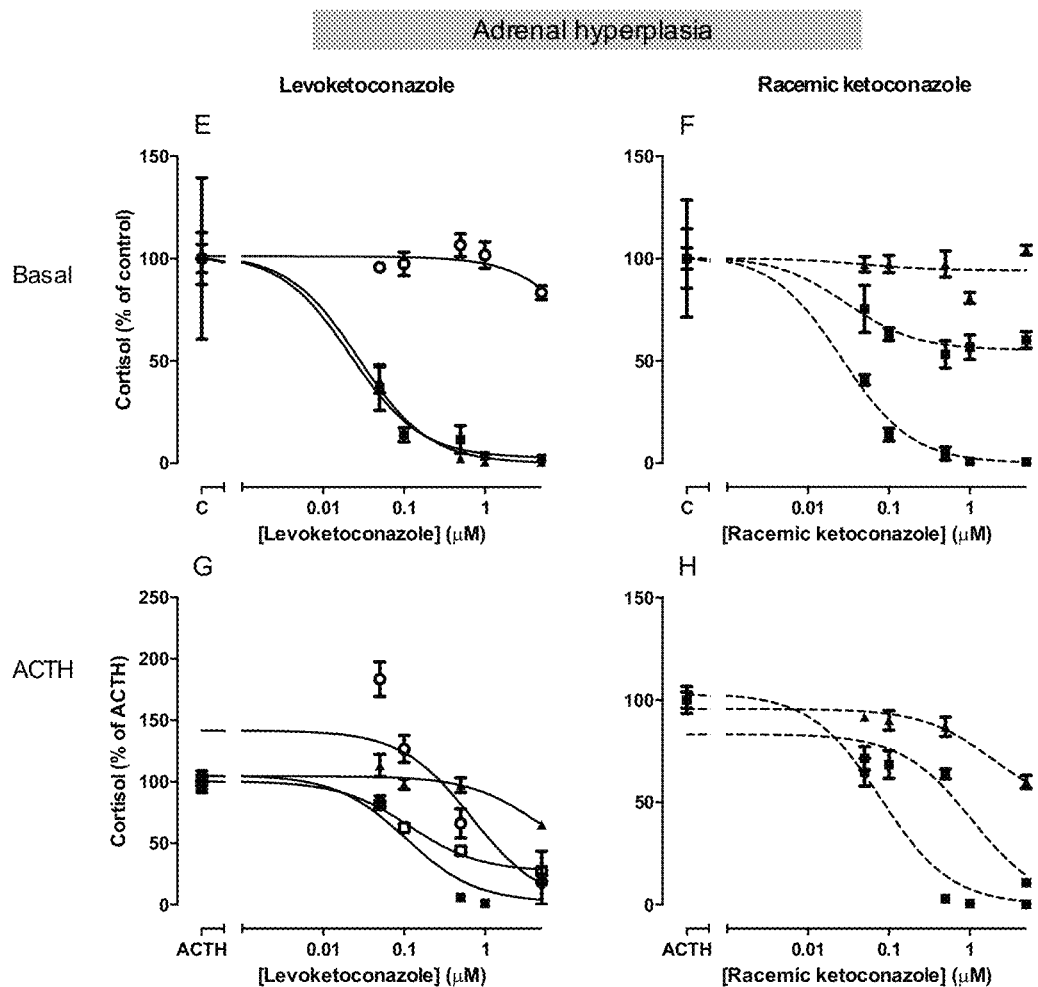
FIG. 2B depicts dose dependent effects of levoketoconazole and racemic ketoconazole on cortisol production in primary adrenal hyperplasia cultures, both ACTH dependent and independent.
Figure 5:
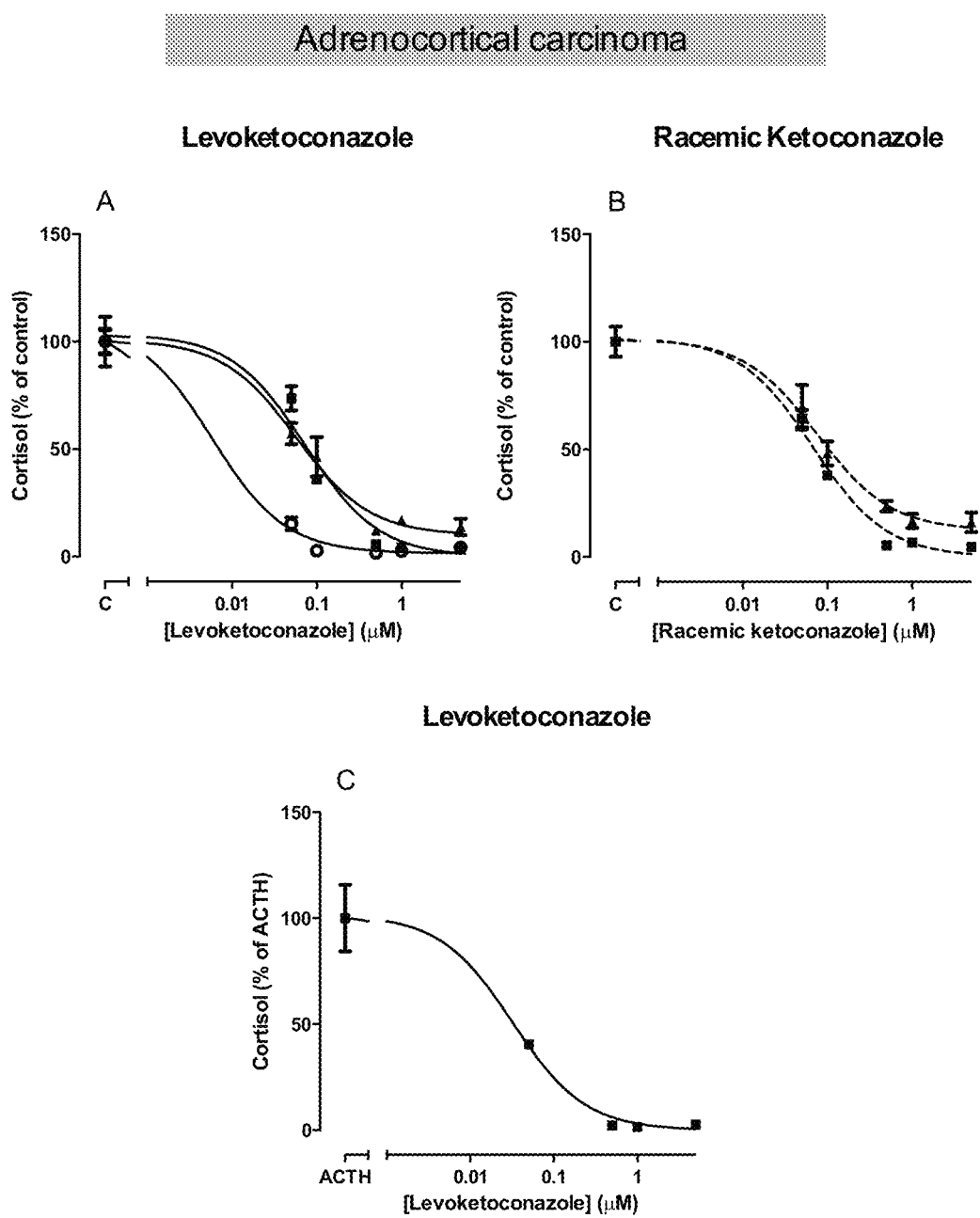
FIG. 5 depicts effects of levoketoconazole and racemic ketoconazole on cortisol production in primary human adrenocortical carcinoma cultures.

$IC_{50}$ values and dose response curves on cortisol production of both levoketoconazole and racemic ketoconazole in the different primary adrenocortical cultures are listed in Table 2 and shown in FIGS. 2A, 2B and 5.

FIGS. 2A and 2B depict dose dependent effects of levoketoconazole (black solid lines) and racemic ketoconazole (black dotted lines) on cortisol production in primary human adrenocortical cultures. FIG. 2A represents cortisol-producing adrenal adenoma cultures, both ACTH dependent and independent. FIG. 2B represents primary adrenal hyperplasia cultures, both ACTH dependent and independent. Controls represent vehicle treatment without or with ACTH stimulation (85 pM). Values are depicted as the mean SEM and as percentage of vehicle treated control. Abbreviations: ACTH, adrenocorticotropic hormone; C, control.

FIG. 5 depicts effects of levoketoconazole (black solid lines) and racemic ketoconazole (black dotted lines) on cortisol production in primary human adrenocortical carcinoma cultures. Controls represent vehicle treatment without (A, B) or with (C) ACTH stimulation (85 pM). Values are depicted as mean SEM and as percentage of vehicle treated control. Abbreviations: ACTH, adrenocorticotropin hormone; C, control.

Figure 3:
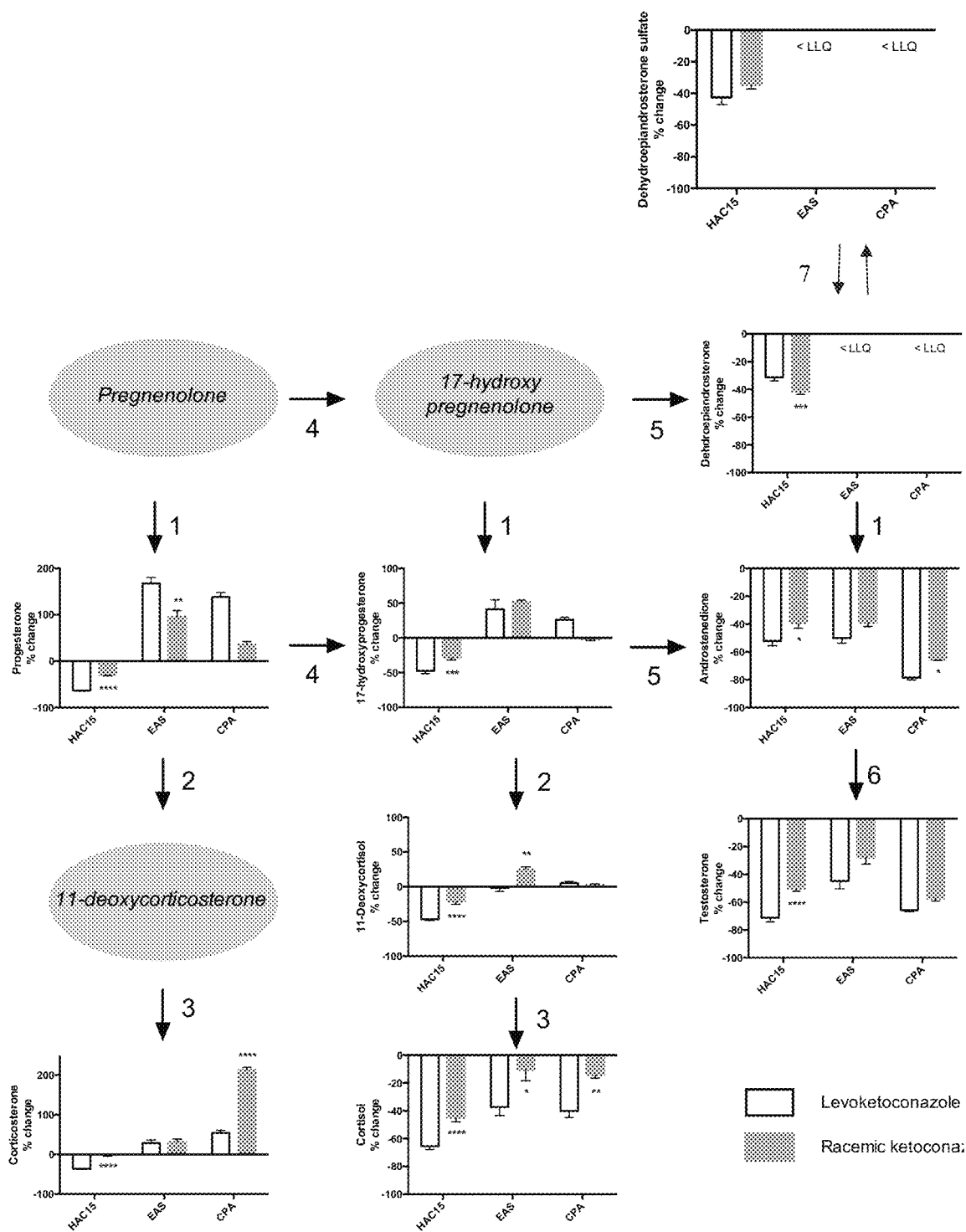
FIG. 3 depicts the effects of levoketoconazole and racemic ketoconazole on the steroid hormone profile in three different adrenocortical cultures.

IC$_{50}$ values for levoketoconazole in the basal condition in CPA primary cultures varied between 0.0631 and 0.140 M, whereas in EAS associated adrenal hyperplasia the two IC$_{50}$ values were lower (0.0220 and 0.0277 µM). In the basal condition, the mean IC$_{50}$ for levoketoconazole was 0.110 µM (95% CI 0.0867-0.139) in ACA (n=4), 0.0257 µM (95% CI 0.0116-0.0569; P<0.0001 vs ACA) in EAS associated adrenal hyperplasia (n=2), and 0.0383 µM (95% CI 0.0253-0.0578; P<0.0001 vs ACA) in ACC (n=3). In six of the ten conditions in which a direct comparison between levoketoconazole and racemic ketoconazole could be made in the same patient, higher IC$_{50}$ values were observed for racemic ketoconazole compared to levoketoconazole (mean increase IC$_{50}$ 52%, range 33-113%). The difference however only reached statistical significance on individual level in one culture (CPA no. 2, P<0.05). In the four remaining cultures, IC$_{50}$ values were highly comparable between both compounds (mean difference in IC$_{50}$ was 5%, range 1-8%). Levoketoconazole also inhibited cortisol production in ACC cultures (FIG. 5). Cortisol production increased in nine of the ten primary cultures with ACTH stimulation, varying from 34% to 2239% (Table 2). In one of the five primary cultures in which basal and ACTH stimulated levoketoconazole IC$_{50}$ values could be compared, a lower IC$_{50}$ value was observed under ACTH stimulation (P=0.0095, ACC no. 3). Effects of Racemic Ketoconazole and Levoketoconazole on the Steroid Hormone Profile on Adrenal Cells
HAC15 Cells To determine the effects of levoketoconazole and racemic ketoconazole on steroid precursors and adrenal androgens as well, multi-steroid analysis was carried out using LC/MS-MS in several conditions and cultures (Table 3). In HAC15 cells, treatment with levoketoconazole resulted in comparable effects on the steroid profile in the basal and ACTH stimulated condition. For instance in the ACTH stimulated condition, production of all steroids was significantly inhibited, including cortisol (−13.81 nmol/L, −31%) and 11-DOC (FIG. 3; −1524 nmol/L, −47%). Except for DHEA and DHEAS, all steroids accumulated under ACTH, varying from an increase of 7% of progesterone, to 359% increase of corticosterone. In both conditions, levoketoconazole inhibited all steroids to a slightly greater extent compared to racemic ketoconazole (FIG. 3. HAC15; all P<0.01), except DHEA, which was more strongly inhibited by racemic ketoconazole (FIG. 3. HAC15; P<0.05). To evaluate the overall effects of the compounds on the steroid profile, absolute changes were added together. The total sum of decrease of steroids was stronger under levoketoconazole compared to racemic ketoconazole treatment (basal: −3,007 vs −1,919 nmol/L; ACTH: −2,811 vs −1,591 nmol/L).

Table 3 presents an overview of effects of levoketoconazole, and racemic ketoconazole on the steroid profile in human adrenocortical cultures. Effects of levoketoconazole (LK) and racemic ketoconazole (RK) on levels of progesterone (prog), corticosterone, 17-hydroxyprogesterone (17-OHP), 11-deoxycortisol (11-DOC), cortisol, dehydroepiandrosterone (DHEA), dehydroepiandrosterone sulfate (DHEAS), androstenedione, and testosterone after 3 days of treatment are shown. Numbers of the primary cultures correspond to the numbers in Table 1 and 2. Data are presented as absolute change±standard error of the difference (in nmol/l) compared to vehicle treated control (basal) or compared to ACTH stimulation with vehicle (ACTH), with percentage change compared to control between brackets. Significant absolute changes compared to control are depicted in bold. * P<0.05,  P<0.01, and * P<0.001 compared to the percentage change by levoketoconazole. Abbreviations include: ACTH, adrenocorticotropin hormone; CPA, cortisol-producing adrenal adenoma; EAS, ectopic ACTH syndrome; LLQ, lower limit of quantitation.

| | | | Prog | Corticosterone | 17-OHP | 11-DOC | Cortisol | DHEA | DHEAS | Androstenedione | Testosterone |
|---|---|---|---|---|---|---|---|---|---|---|---|
| HAC15 | Basal | LK 0.5 µM | −0.9125 ± 0.06461 (−55%) | −0.2938 ± 0.1046 (−39%) | −26.89 ± 1.688 (−57%) | −1129 ± 118.9 (−48%) | −16.36 ± 1.092 (−69%) | −31.04 ± 2.496 (−44%) | −658.6 ± 68.10 (−56%) | −1105 ± 117.2 (−56%) | −39.19 ± 5.124 (−64%) |
| | | RK 0.5 µM | −0.3125 ± 0.07948 (−19%****) | +0.1750 ± 0.09978 (+19%****) | −16.50 ± 2.053 (−37%****) | −521.2 ± 111.9 (−23%****) | −10.93 ± 0.7632 (−47%****) | −39.50 ± 2.643 (−56%**) | −496.4 ± 37.69 (−44%*) | −809.0 ± 80.32 (−47%**) | −25.78 ± 2.450 (−58%***) |
| | ACTH | LK 0.5 µM | −2.163 ± 0.09246 (−64%) | −1.063 ± 0.1457 (−36%) | −24.73 ± 2.661 (−47%) | −1524 ± 70.93 (−47%) | −21.80 ± 1.260 (−65%) | −13.81 ± 1.794 (−31%) | −250.1 ± 33.78 (−43%) | −943.7 ± 78.73 (−52%) | −30.52 ± 2.117 (−71%) |
| | | RK 0.5 µM | −0.9625 ± 0.1238 (−30%****) | −0.01250 ± 0.3414 (−1.5%****) | −14.13 ± 1.700 (−29%***) | −664.5 ± 114.8 (−22%****) | −15.15 ± 1.411 (−45%****) | −17.04 ± 2.702 (−41%***) | −197.4 ± 21.52 (−35%) | −661.4 ± 66.98 (−40%*) | −20.29 ± 1.360 (−50%****) |
| EAS associated adrenal hyperplasia no. 1 | Basal | LK 0.05 µM | +5.108 ± 0.8569 (+123%) | −67.07 ± 69.28 (−33%) | −0.4667 ± 1.087 (−4.6%) | −96.33 ± 24.22 (−37%) | −178.4 ± 78.74 (−64%) | <LLQ | <LLQ | −6.508 ± 1.193 (−64%) | −0.2583 ± 0.07949 (−48%) |
| | | RK 0.05 µM | +4.475 ± 0.6719 (+108%) | −68.60 ± 71.34 (−32%) | +0.6833 ± 0.9451 (+7.5%) | −62.23 ± 18.50 (−27%) | −86.78 ± 22.08 (−57%) | <LLQ | <LLQ | −5.850 ± 1.246 (−55%) | −0.1500 ± 0.05401 (−32%) |
| | | LK 5 µM | +13.36 ± 0.4985 (+363%) | −193.8 ± 47.52 (−99%) | −14.33 ± 0.2962 (−93%) | −280.5 ± 16.84 (−99%) | −230.3 ± 71.36 (−99%) | <LLQ | <LLQ | −7.978 ± 0.8186 (−95%) | −0.3838 ± 0.07702 (−90%) |
| | | RK 5 µM | +19.89 ± 1.415 (+537%***) | −166.5 ± 6.258 (−98%) | −15.07 ± 0.7918 (−92%) | −270.7 ± 18.04 (−98%) | −165.2 ± 16.30 (−99%) | <LLQ | <LLQ | −8.219 ± 0.9984 (−94%) | −0.2688 ± 0.07031 (−66%) |
| | ACTH | LK 0.05 µM | +6.025 ± 0.5089 (+167%) | 97.95 ± 27.79 (+29%) | +8.300 ± 2.815 (+41%) | −6.000 ± 22.72 (+1.6%) | −234.8 ± 44.70 (−37%) | <LLQ | <LLQ | −9.600 ± 1.009 (−50%) | −0.3250 ± 0.07500 (−45%) |
| | | RK 0.05 µM | +3.425 ± 0.5483 (+96%**) | +105.7 ± 32.29 (+31%) | +8.133 ± 1.116 (+52%) | +76.63 ± 23.14 (+25%**) | −62.25 ± 66.33 (−11%*) | <LLQ | <LLQ | −7.475 ± 1.528 (−39%) | −0.1750 ± 0.05590 (−28%) |
| | | LK 5 µM | +37.66 ± 3.768 (+1201%) | −373.7 ± 9.451 (−100%) | −31.55 ± 1.562 (−90%) | −435.4 ± 14.40 (−99%) | −640.2 ± 11.97 (−100%) | <LLQ | <LLQ | −15.19 ± 0.6004 (−98%) | −0.5513 ± 0.05702 (−85%) |

-continued

| | | | Prog | Corticosterone | 17-OHP | 11-DOC | Cortisol | DHEA | DHEAS | Androstenedione | Testosterone |
|---|---|---|---|---|---|---|---|---|---|---|---|
| | | RK 5 µM | +39.86 ± 3.290 (+1292%) | −397.6 ± 6.733 (−100%) | −28.44 ± 1.132 (−90%) | −402.7 ± 11.07 (−99%) | −643.5 ± 63.91 (−100%) | <LLQ | <LLQ | −14.79 ± 1.146 (−98%) | −0.4350 ± 0.03253 (−85%) |
| CPA no. 2 | Basal | LK 0.1 µM | +2.350 ± 0.2255 (+138%) | +49.50 ± 6.455 (+54%) | +5.125 ± 0.8538 (+26%) | +14.80 ± 5.780 (+5.4%) | −264.2 ± 40.21 (−40%) | <LLQ | <LLQ | −36.68 ± 1.657 (−79%) | −0.3750 ± 0.03096 (−66%) |
| | | RK 0.1 µM | +0.5167 ± 0.1263 (+36%) | +175.8 ± 5.566 (+213%****) | −0.4750 ± 0.5893 (−2.4%) | +6.400 ± 9.332 (+2.4%) | −92.95 ± 40.07 (−14%**) | <LLQ | <LLQ | −32.85 2.200 (−66%*) | −0.3250 ± 0.02300 (−57%) |
| | | LK 0.5 µM | +39.95 ± 1.764 (+2350%) | +218.0 ± 3.773 (+239%) | +21.28 ± 3.917 (+107%) | −98.25 ± 5.847 (−36%) | −633.3 ± 24.92 (−96%) | <LLQ | <LLQ | −45.18 ± 1.470 (−97%) | −0.4725 ± 0.03038 (−83%) |
| | | RK 0.5 µM | +22.47 ± 1.098 (+1567%) | +143.8 ± 23.99 (+174%*) | +11.45 ± 1 .992 (+58%*) | −37.70 ± 17.36 (−14%***) | −562.7 ± 40.11 (−87%) | <LLQ | <LLQ | −47.28 ± 2.215 (−95%) | −0.4475 ± 0.02175 (−79%) |

ACTH-Dependent Adrenal Hyperplasia

The effects of two concentrations (0.05 and 5 µM) of both levoketoconazole and racemic ketoconazole on the steroid profile were studied in EAS associated adrenal hyperplasia no. 1, resulting in a dose-dependent effect on the components of the steroid profile (Table 3). DHEA and DHEAS were below the limit of quantitation.

FIG. 3 depicts the effects of levoketoconazole (white bars) and racemic ketoconazole (grey bars) on the steroid hormone profile in three different adrenocortical cultures. The displayed conditions were chosen based on the most pronounced differences between levoketoconazole and racemic ketoconazole and were different for HAC15 (ACTH stimulation, concentration 0.5 µM), ectopic ACTH syndrome associated adrenal hyperplasia no. 1 (EAS; ACTH stimulation, concentration 0.05 µM) and cortisol-producing adenoma no. 2 (CPA; basal condition, concentration 0.1 µM). Numbers of the primary cultures correspond to the numbers in Table 1 and 2. Arrows represent members of the cytochrome P450 family of enzymes: (1) 3β-hydroxysteroid dehydrogenase, (2) 21-hydroxylase, (3) 1β-hydroxylase, (4) 17α-hydroxylase, (5) 17,20-lyase, (6) 17β-hydroxysteroid dehydrogenase III, and (7) sulfotransferase. Values are depicted as the percentage change SEM compared to ACTH stimulation (HAC15 and EAS associated hyperplasia) or vehicle treated control (CPA). Note the differences in scale of the y-axis. ACTH, adrenocorticotropic hormone; LLQ, lower limit of quantitation. * P<0.05,  P<0.01, * P<0.001, and **** P<0.0001 vs the effect of levoketoconazole.

In this primary culture, ACTH stimulation resulted in an increase of corticosterone, 17-OHP, 11-DOC, cortisol, and androstenedione (mean increase+111%). Progesterone slightly decreased (−11%), whereas testosterone did not change. In the ACTH stimulated condition at a concentration of 0.5 µM (FIG. 3 EAS), levoketoconazole significantly inhibited cortisol (−234.8 nmol/L, −37%, P=0.0019), androstenedione (−9.600 nmol/L, −50%; P<0.0001), and testosterone (−0.3250 nmol/L, −45%, P=0.0049 vs control). In contrast to the basal condition, corticosterone and 17-OHP accumulated after treatment with levoketoconazole (+97.95 nmol/L, +29%, P=0.0124; +8.300 nmol/L, +41%, P=0.0257; respectively), whereas 11-DOC did not change (FIG. 3. EAS). When focusing on the difference between levoketoconazole and racemic ketoconazole, accumulation of progesterone (+167% vs +96%; P<0.01), and decrease of cortisol (−37% vs −11%; P<0.05) were more strongly evident after exposure to levoketoconazole (FIG. 3. EAS). Accumulation of 11-DOC was in contrast higher under racemic ketoconazole (P<0.01 vs levoketoconazole). In the basal condition at 0.5 M, no significant changes between both compounds were observed (Table 3). The total change of steroids in the basal condition was comparable between levoketoconazole and racemic ketoconazole (−343.9 vs −218.5 nmol/L, respectively), whereas under ACTH stimulation, the total sum of change of the steroids was a decrease of 138.5 nmol/L under levoketoconazole, whereas there was an increase of 124.0 nmol/L by racemic ketoconazole.

At a hundred times higher concentration of 5 µM of the drugs, all steroids except progesterone were strongly inhibited by levoketoconazole and racemic ketoconazole (all decrease >66%; Table 3) both in the basal as the ACTH stimulated condition. In both conditions, the total sum of change of the steroids was comparable between levoketoconazole and racemic ketoconazole.

Cortisol-Producing Adrenal Adenoma

In CPA primary culture no. 2, two concentrations (0.1 and 0.5 µM) of levoketoconazole and racemic ketoconazole were tested in the basal condition, which also resulted in a dose-dependent effect on the steroid profile (Table 3). At 0.1 µM, levoketoconazole inhibited cortisol (−264.2 nmol/L, −40%, P=0.0006), androstenedione (−36.68 nmol/L, −79%, P<0.0001), and testosterone (−0.3750 nmol/L, −66%, P<0.0001), whereas the other steroids increased (Table 3; FIG. 3. CPA). Levoketoconazole inhibited cortisol and androstenedione more potent compared to racemic ketoconazole (−40% vs −14%, P<0.01; −79% vs −66%, P<0.05; respectively), while corticosterone accumulated more strongly under racemic ketoconazole (+54% vs +213%, P<0.0001; FIG. 3 CPA). The total change of steroids at 0.1 µM was a decrease of 229.5 nmol/L under levoketoconazole, whereas there was an increase of 55.6 nmol/L by racemic ketoconazole. At a five times higher concentration of 0.5 µM, the same tendency was observed, although with a more pronounced absolute change of all steroids in both up- and downwards directions by both compounds (Table 3). No difference was observed in the total sum of change of the steroids between levoketoconazole and racemic ketoconazole.

Figure 4A:
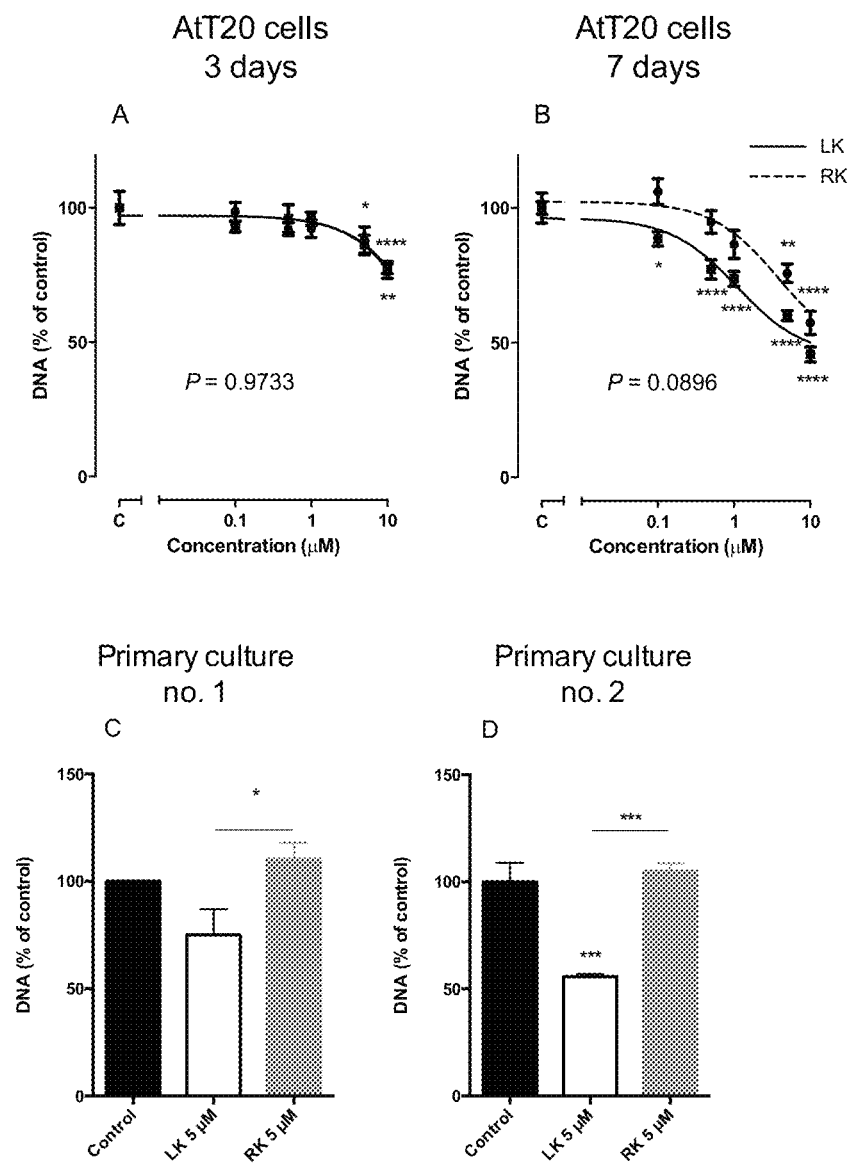
FIGS. 4A and 4B depict the effects of levoketoconazole and racemic ketoconazole on cell amount and ACTH secretion corrected for cell amount in mouse pituitary AtT20 cells and in two primary human corticotroph pituitary adenoma cultures.
Figure 4B:
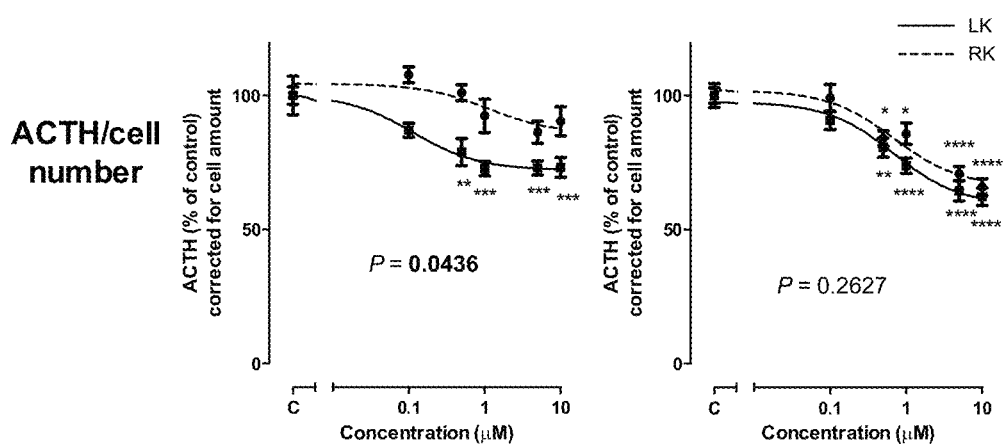
Figure 4B:
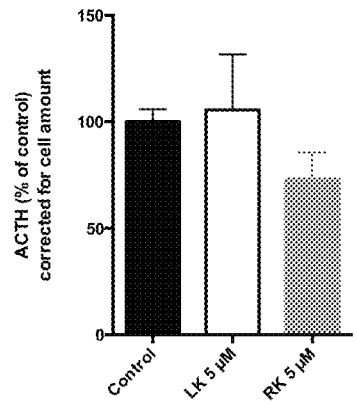
Figure 4B:
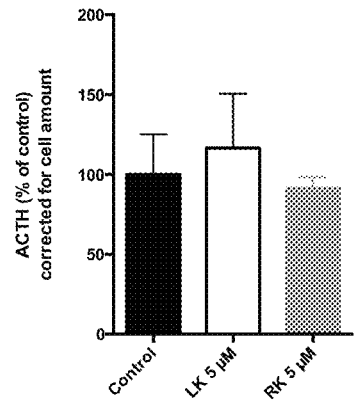

Effects of Levoketoconazole and Racemic Ketoconazole on Corticotroph Pituitary Cells FIGS. 4A and 4B depict the effects of levoketoconazole (LK) and racemic ketoconazole (RK) on cell amount (FIG. 4A) and ACTH secretion corrected for cell amount (FIG. 4B) in mouse pituitary AtT20 cells and in two primary human corticotroph pituitary adenoma cultures. Black solid lines represent treatment with levoketoconazole, black dotted lines represent treatment with racemic ketoconazole. Primary cultures were incubated with treatment for 7 days. Values are depicted as the mean SEM and as percentage of vehicle treated control. P-values compare dose response curves of levoketoconazole and racemic ketoconazole in AtT20 cells. * P<0.05,  P<0.01, * P<0.001, and **** P<0.0001 vs control or as stated by the lines.

Levoketoconazole and racemic ketoconazole inhibited cell number after 3 and 7 days of treatment in corticotroph pituitary AtT20 cells, whereas no effect was seen after 24 h of treatment (data not shown). $IC_{50}$ values for inhibition of cell number after 7 days were 1.05 μM (95% CI 0.576-1.909) and 5.81 μM (95% CI 0.948-35.48) for levoketoconazole and racemic ketoconazole, respectively (P=0.0892). Only levoketoconazole showed inhibition of ACTH secretion, corrected for cell amount, after 3 days of treatment (P=0.0436 vs racemic ketoconazole), where both levoketoconazole and racemic ketoconazole inhibited ACTH secretion after 7 days of treatment (FIG. 4B). Maximal inhibition of ACTH secretion after 7 days of treatment with 10 μM was 38% and 34% for levoketoconazole and racemic ketoconazole, respectively (FIG. 4B).

In two primary ACTH-secreting corticotroph pituitary adenoma cultures, the effects of levoketoconazole and racemic ketoconazole were examined on both cell amount and ACTH secretion after 7 days of treatment. In primary culture no. 2, levoketoconazole significantly inhibited cell number after 7 days of treatment (P<0.001 vs control; FIG. 4A). In both cultures, there was a significant difference between levoketoconazole and racemic ketoconazole, favoring a stronger effect by levoketoconazole (FIG. 4A). No effects were observed on ACTH secretion corrected for cell number after 7 days of treatment in both primary cultures (FIG. 4B).

DISCUSSION

We show that levoketoconazole is a potent inhibitor of cortisol secretion and might be slightly more potent compared to racemic ketoconazole in vitro.

In primary human adrenocortical cultures, levoketoconazole appears to be a potent inhibitor of cortisol secretion. Sensitivity to levoketoconazole seems to be slightly higher compared to racemic ketoconazole in primary cultures as well. We also demonstrate that potency of levoketoconazole is highly variable between patients and tissue specimens with a 24-fold difference in $IC_{50}$ value, indicating that there might also be heterogeneity in response to levoketoconazole in clinical studies, due to differences in sensitivity at tissue level.

We show that effects of levoketoconazole on the steroid profile are variable among patients; in some cases all steroids are inhibited, whereas in other cultures there is accumulation of progesterone, corticosterone, 17-OHP, and 11-DOC. These differences might be related to differences in tissue specimens. The changes on the steroid profile suggest that levoketoconazole inhibits several steroidogenic enzymes and that effects of levoketoconazole and racemic ketoconazole seem overall comparable. Differences in percentage change are subtle, favoring a more potent effect of levoketoconazole compared to racemic ketoconazole. In HAC15 cells, adrenal androgens are inhibited more strongly by levoketoconazole, whereas this was not confirmed in most of the primary human adrenocortical cultures. The absence of strong accumulation equal to the total sum of inhibition of steroids, suggests an inhibition of the proximal steps of the steroid biosynthetic pathway, like cholesterol side chain cleavage enzyme or steroidogenic acute regulatory protein (StAR). We hypothesize that the extent of this proximal inhibition might be slightly higher for levoketoconazole compared to racemic ketoconazole, as demonstrated by a greater negative balance for levoketoconazole in the majority of adrenal cultures.

In the EAS associated adrenal hyperplasia, corticosterone accumulated at 0.05 μM and decreased at 5 μM levoketoconazole and racemic ketoconazole under ACTH stimulation. This implies that specificity of levoketoconazole and racemic ketoconazole on inhibition of steroidogenesis enzymes is dependent on concentration.

We show that both levoketoconazole and racemic ketoconazole affect corticotroph ACTH secreting cells. In this study, levoketoconazole and racemic ketoconazole inhibited cell growth and ACTH production corrected for cell amount in a dose- and time dependent manner in AtT20 cells. Thereby, in one of the two human corticotroph pituitary adenoma cultures, levoketoconazole inhibited cell amount, whereas this effect was not observed after treatment with racemic ketoconazole. No effect was observed on ACTH secretion in these two corticotroph pituitary adenoma cultures, which might be due to the applied correction for cell amount, which has not been done in previous studies. This suggests that the inhibitory corticotroph effects in primary cultures could be primarily cytotoxic.

In conclusion, we show that levoketoconazole is a potent inhibitor of cortisol secretion in primary human adrenocortical cells and might inhibit steroidogenesis slightly more potent compared to racemic ketoconazole. Together with the previously reported potential advantages of increased efficacy in vivo, a favorable safety profile and increased therapeutic index, this makes levoketoconazole a very promising novel treatment option for Cushing's syndrome. In addition, levoketoconazole may have pituitary-directed effects.

What is claimed is:

1. A method for treating congenital adrenal hyperplasia in a subject in need thereof, comprising administering to said subject a therapeutically effective amount of 2S,4R ketoconazole enantiomer, wherein the ketoconazole content of the therapeutically effective amount comprises less than 20% 2R,4S enantiomer and more than 80% 2S,4R enantiomer, and wherein 11-deoxycortisol (11-DOC) secretion is not substantially increased after administration of the 2S, 4R ketoconazole enantiomer.

2. The method of claim 1, wherein the congenital adrenal hyperplasia is due to 11-hydroxylase deficiency.

3. The method of claim 2, wherein the congenital adrenal hyperplasia is of the classic form.

4. The method of claim 1, wherein the therapeutically effective amount of the 2S,4R ketoconazole enantiomer is from about 50 mg to about 600 mg.

5. The method of claim 1, wherein the therapeutically effective amount of the 2S,4R ketoconazole enantiomer is co-administered with one or more other active compounds selected from the group consisting of biguanides, sulfonylureas, HMG-COA reductase inhibitors, PPAR agonists, PTP-1B inhibitors, DPP-IV inhibitors, and anti-obesity compounds.

6. A composition for use in the method of claim 1, the composition comprising a therapeutically effective amount of the 2S,4R ketoconazole enantiomer, wherein the ketoconazole content of the therapeutically effective amount comprises less than 20% 2R,4S enantiomer and more than 80% 2S,4R enantiomer.

7. The composition of claim 6, wherein the therapeutically effective amount of the 2S,4R ketoconazole enantiomer is from about 50 mg to about 600 mg.

8. The composition of claim 6, wherein the congenital adrenal hyperplasia is due to 11-hydroxylase deficiency.

9. The composition of claim 8, wherein the congenital adrenal hyperplasia is of the classic form.

10. The composition of claim 6, further comprising one or more active compounds other than the therapeutically effective amount of 2S,4R ketoconazole enantiomer, selected from the group consisting of biguanides, sulfonylureas, HMG-COA reductase inhibitors, PPAR agonists, PTP-1B inhibitors, DPP-IV inhibitors, and anti-obesity compounds.

11. A method for treating primary aldosteronism in a subject in need thereof, comprising administering to said subject a therapeutically effective amount of 2S,4R ketoconazole enantiomer, wherein the ketoconazole content of the therapeutically effective amount comprises less than 20% of 2R,4S enantiomer and more than 80% of 2S,4R enantiomer, and wherein 11-DOC secretion is not substantially increased after administration of the 2S, 4R ketoconazole enantiomer.

12. The method of claim 11, wherein the therapeutically effective amount of the 2S,4R ketoconazole enantiomer is from about 50 mg to about 600 mg.

13. The method of claim 11, wherein the therapeutically effective amount of the 2S,4R ketoconazole enantiomer is co-administered with one or more other active compounds selected from the group consisting of biguanides, sulfonylureas, HMG-COA reductase inhibitors, PPAR agonists, PTP-1B inhibitors, DPP-IV inhibitors, and anti-obesity compounds.

14. A composition for use in the method of claim 11, the composition comprising a therapeutically effective amount of the 2S,4R ketoconazole enantiomer, wherein the ketoconazole content of the therapeutically effective amount comprises less than 20% 2R,4S enantiomer and more than 80% 2S,4R enantiomer.

15. The composition of claim 14, wherein the therapeutically effective amount of the 2S,4R ketoconazole enantiomer is from about 50 mg to about 600 mg.

16. The composition of claim 14, further comprising one or more active compounds other than the therapeutically effective amount of 2S,4R ketoconazole enantiomer, selected from the group consisting of biguanides, sulfonylureas, HMG-COA reductase inhibitors, PPAR agonists, PTP-1B inhibitors, DPP-IV inhibitors, and anti-obesity compounds.

* * * * *